(12) United States Patent
Domon et al.

(10) Patent No.: US 11,429,023 B2
(45) Date of Patent: Aug. 30, 2022

(54) ONIUM SALT, NEGATIVE RESIST COMPOSITION, AND RESIST PATTERN FORMING PROCESS

(71) Applicant: Shin-Etsu Chemical Co., Ltd., Tokyo (JP)

(72) Inventors: Daisuke Domon, Joetsu (JP); Naoya Inoue, Joetsu (JP); Masaki Ohashi, Joetsu (JP); Keiichi Masunaga, Joetsu (JP); Masaaki Kotake, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 292 days.

(21) Appl. No.: 16/655,571

(22) Filed: Oct. 17, 2019

(65) Prior Publication Data
US 2020/0133121 A1 Apr. 30, 2020

(51) Int. Cl.
| | | |
|---|---|---|
| *G03F 7/004* | (2006.01) | |
| *C07C 311/48* | (2006.01) | |
| *C07C 381/12* | (2006.01) | |
| *G03F 1/50* | (2012.01) | |
| *G03F 1/76* | (2012.01) | |
| *G03F 1/78* | (2012.01) | |
| *G03F 7/038* | (2006.01) | |
| *G03F 7/16* | (2006.01) | |
| *G03F 7/20* | (2006.01) | |
| *G03F 7/32* | (2006.01) | |
| *G03F 7/38* | (2006.01) | |

(52) U.S. Cl.
CPC .......... *G03F 7/0045* (2013.01); *C07C 311/48* (2013.01); *C07C 381/12* (2013.01); *G03F 1/50* (2013.01); *G03F 1/76* (2013.01); *G03F 1/78* (2013.01); *G03F 7/038* (2013.01); *C07C 2601/14* (2017.05); *G03F 7/162* (2013.01); *G03F 7/168* (2013.01); *G03F 7/2004* (2013.01); *G03F 7/2037* (2013.01); *G03F 7/322* (2013.01); *G03F 7/38* (2013.01)

(58) Field of Classification Search
CPC ... C07C 311/48; C07C 381/12; C08F 220/30; G03F 7/004; G03F 7/038; G03F 7/168; G03F 7/162; G03F 7/322; G03F 7/2004; G03F 7/2037; G03F 7/38
See application file for complete search history.

(56) References Cited

U.S. PATENT DOCUMENTS

| | | |
|---|---|---|
| 5,286,600 A | 2/1994 | Ochiai et al. |
| 5,618,892 A | 4/1997 | Furihata et al. |
| 6,479,210 B2 | 11/2002 | Kinoshita et al. |
| 6,485,883 B2 | 11/2002 | Kodama et al. |
| 6,492,091 B2 | 12/2002 | Kodama et al. |
| 6,506,534 B1 | 1/2003 | Nozaki et al. |
| 6,605,409 B2 | 8/2003 | Kodama et al. |
| 7,214,467 B2 | 5/2007 | Kanna et al. |
| 7,300,739 B2 | 11/2007 | Allen et al. |
| 7,393,624 B2 | 7/2008 | Allen et al. |
| 7,563,558 B2 | 7/2009 | Allen et al. |
| 8,168,367 B2 | 5/2012 | Watanabe et al. |
| 8,361,692 B2 | 1/2013 | Tanaka et al. |
| 8,361,693 B2 | 1/2013 | Masunaga et al. |
| 8,637,222 B2* | 1/2014 | Tsuchihashi .......... G03F 7/0382 430/296 |
| 8,685,616 B2* | 4/2014 | Gonsalves ............ G03F 7/0397 430/270.1 |
| 8,900,791 B2 | 12/2014 | Tsuchimura et al. |
| 9,023,581 B2* | 5/2015 | Kawaue ................ C07C 309/10 430/270.1 |
| 9,023,587 B2* | 5/2015 | Hatakeyama ........... C08F 18/04 430/270.1 |
| 9,075,306 B2 | 7/2015 | Takeda et al. |
| 9,551,928 B2* | 1/2017 | Yamaguchi .......... G03F 7/0045 |
| 9,599,897 B2* | 3/2017 | Nishimura ................ G03F 7/32 |
| 9,604,921 B2 | 3/2017 | Domon et al. |
| 9,645,493 B2 | 5/2017 | Domon et al. |
| 9,703,193 B2* | 7/2017 | Fujiwara .............. C07D 303/16 |
| 9,904,172 B2 | 2/2018 | Kumaki et al. |
| 9,958,775 B2 | 5/2018 | Tsuruta et al. |
| 9,969,829 B2* | 5/2018 | Domon ................ C08F 220/30 |
| 10,054,853 B2* | 8/2018 | Fujiwara ................... G03F 7/38 |
| 10,120,279 B2 | 11/2018 | Masunaga et al. |
| 10,310,375 B2* | 6/2019 | Gonsalves ............ C07C 311/48 |

(Continued)

FOREIGN PATENT DOCUMENTS

| | | |
|---|---|---|
| EP | 0 208 353 A1 | 1/1987 |
| EP | 1 158 363 A1 | 11/2001 |

(Continued)

OTHER PUBLICATIONS

Machine translation of JP 2013-164588 (no date).*
Machine translation of JP 2008-249951 (no date).*
Office Action dated May 29, 2020, issued in counterpart TW Application No. 108137972 (7 pages).
Office Action dated Jan. 25, 2021, issued in counterpart KR Application No. 10-2019-0133672. (6 pages).
Office Action dated Aug. 17, 2021, issued in counterpart JP application No. 2018-200797, with English translation. (6 pages).
Machine translation of JP 2003-337414; Cited in Final US Office Action dated Feb. 15, 2022.

(Continued)

*Primary Examiner* — Amanda C. Walke
(74) *Attorney, Agent, or Firm* — WHDA, LLP

(57) ABSTRACT

A negative resist composition comprising an onium salt having formula (A) and a base polymer is provided. The resist composition exhibits a high resolution during pattern formation and forms a pattern with minimal LER.

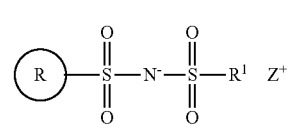

(A)

18 Claims, No Drawings

(56) References Cited

U.S. PATENT DOCUMENTS

| | | | |
|---|---|---|---|
| 10,466,588 B2* | 11/2019 | Liu | G03F 7/162 |
| 10,606,172 B2* | 3/2020 | Hatakeyama | C08F 222/24 |
| 10,725,377 B2 | 7/2020 | Kotake et al. | |
| 11,231,650 B2 | 1/2022 | Kotake et al. | |
| 2006/0166133 A1 | 7/2006 | Koitabashi et al. | |
| 2009/0226843 A1* | 9/2009 | Hatakeyama | G03F 7/0397 |
| | | | 430/286.1 |
| 2010/0323305 A1* | 12/2010 | Tsubaki | G03F 7/325 |
| | | | 430/325 |
| 2012/0321855 A1* | 12/2012 | Iwato | G03F 7/30 |
| | | | 428/156 |
| 2012/0322007 A1* | 12/2012 | Kato | G03F 7/0382 |
| | | | 430/285.1 |
| 2013/0017377 A1 | 1/2013 | Kataoka et al. | |
| 2013/0089819 A1* | 4/2013 | Kawaue | C07C 309/09 |
| | | | 430/285.1 |
| 2013/0209922 A1 | 8/2013 | Masunaga et al. | |
| 2014/0212810 A1 | 7/2014 | Hatakeyama et al. | |
| 2015/0086912 A1* | 3/2015 | Kawabata | C08F 212/30 |
| | | | 430/18 |
| 2015/0234278 A1 | 8/2015 | Hatakeyama et al. | |
| 2015/0268556 A1 | 9/2015 | Domon et al. | |
| 2016/0090355 A1 | 3/2016 | Domon et al. | |
| 2016/0229940 A1 | 8/2016 | Hatakeyama et al. | |
| 2016/0299428 A1 | 10/2016 | Masunaga et al. | |
| 2016/0299430 A1 | 10/2016 | Domon et al. | |
| 2016/0299431 A1 | 10/2016 | Adachi et al. | |
| 2016/0320698 A1 | 11/2016 | Fujiwara et al. | |
| 2016/0342086 A1 | 11/2016 | Sagehashi et al. | |
| 2016/0349612 A1 | 12/2016 | Fujiwara et al. | |
| 2017/0210836 A1 | 7/2017 | Domon et al. | |
| 2017/0355795 A1 | 12/2017 | Hatakeyama et al. | |
| 2018/0039175 A1 | 2/2018 | Masunaga et al. | |
| 2018/0039185 A1 | 2/2018 | Ebihara | |
| 2018/0180998 A1 | 6/2018 | Kotake et al. | |
| 2018/0210338 A1 | 7/2018 | Yahagi et al. | |
| 2019/0018319 A1 | 1/2019 | Yamazaki et al. | |
| 2019/0361348 A1 | 11/2019 | Kotake et al. | |
| 2020/0133121 A1 | 4/2020 | Domon et al. | |
| 2020/0301274 A1 | 9/2020 | Taniguchi et al. | |
| 2020/0301275 A1 | 9/2020 | Taniguchi et al. | |

FOREIGN PATENT DOCUMENTS

| | | | | |
|---|---|---|---|---|
| EP | 1 684 118 | A1 | 7/2006 | |
| EP | 1 975 711 | A1 | 10/2008 | |
| EP | 2264525 | A2 | 12/2010 | |
| EP | 2328864 | A1 | 6/2011 | |
| EP | 2626743 | A1 | 8/2013 | |
| EP | 3 032 333 | A2 | 6/2016 | |
| JP | H5-232702 | A | 9/1993 | |
| JP | H08-202037 | A | 8/1996 | |
| JP | 11-327143 | A | 11/1999 | |
| JP | 2001-154357 | A | 6/2001 | |
| JP | 2001-226430 | A | 8/2001 | |
| JP | 2001-330947 | A | 11/2001 | |
| JP | 2002-060361 | A | 2/2002 | |
| JP | 2003-337414 | A | 11/2003 | |
| JP | 2006-201532 | A | 8/2006 | |
| JP | 2006-215180 | A | 8/2006 | |
| JP | 3955384 | B2 | 8/2007 | |
| JP | 4116340 | B2 | 7/2008 | |
| JP | 2008-249762 | A | 10/2008 | |
| JP | 2008249951 | A * | 10/2008 | G03F 7/0382 |
| JP | 4226803 | B2 | 2/2009 | |
| JP | 2009-53518 | A | 3/2009 | |
| JP | 4231622 | B2 | 3/2009 | |
| JP | 2009-251037 | A | 10/2009 | |
| JP | 2010-100604 | A | 5/2010 | |
| JP | 2010-164933 | A | 7/2010 | |
| JP | 2010-276910 | A | 12/2010 | |
| JP | 2011-22564 | A | 2/2011 | |
| JP | 2011-203644 | A | 10/2011 | |
| JP | 5083528 | B2 | 11/2012 | |
| JP | 2013164588 | A * | 8/2013 | G03F 7/0382 |
| JP | 5376847 | B2 * | 12/2013 | |
| JP | 2016-200651 | A | 12/2016 | |
| JP | 2016-210761 | A | 12/2016 | |
| JP | 2017-16068 | A | 1/2017 | |
| JP | 2017-132827 | A | 8/2017 | |
| JP | 6248882 | B2 | 12/2017 | |
| JP | 6658204 | B2 * | 3/2020 | C07D 305/08 |
| KR | 10-2016-0140460 | A | 12/2016 | |
| KR | 10-2018-0077073 | A | 7/2018 | |
| TW | 201617313 | A | 5/2016 | |
| TW | 201642042 | A | 12/2016 | |
| TW | 201812450 | A | 4/2018 | |
| WO | 2016/038476 | A1 | 3/2016 | |

OTHER PUBLICATIONS

Final Office Action dated Feb. 15, 2022, issued in U.S. Appl. No. 16/417,909 (26 pages).

Ito et al., "Negative Resist Compositions," IBM Technical Disclosure Bulletin vol. 35, No. 1B, Jun. 1992, p. 397.

Ito et al., "Acid-Catalyzed Dehydration, A New Mechanism for Chemically Amplified Lithographic Imaging," ACS Symposium Series 537, Chapter 5, 1994, p. 64-87.

Yoshida et al., "Cationic chemistry and chemically amplified resist materials for microlithography; synthesis and applcations of copolymers of 4-(1-hydroxy-1-methylethyl) styrene and styrene or 4-hydroxystyrene," Polymer, vol. 35, No. 1, 1994, p. 5-13.

European Search Report dated Oct. 28, 2019, issued in EP application No. 19173980.4 (counterpart to U.S. Appl. No. 16/417,909: (10 pages).

Office Action dated Apr. 13, 2021, issued in JP Application No. 2018-100615, with English translation. (counterpart to U.S. Appl. No. 16/417,909: (5 pages).

Office Action dated Jul. 9, 2020, issued in counterpart TW Application No. 108117419 (counterpart to U.S. Appl. No. 16/419,331: (11 pages).

Non-Final Action dated Nov. 1, 2021, issued in U.S. Appl. No. 16/417,909 (34 pages).

Non-Final Action dated Jun. 9, 2021, issued in U.S. Appl. No. 16/419,331 (25 pages).

Non-Final Office Action dated May 31, 2022, issued in U.S. Appl. No. 16/417,909 (11 pages).

\* cited by examiner

ONIUM SALT, NEGATIVE RESIST COMPOSITION, AND RESIST PATTERN FORMING PROCESS

CROSS-REFERENCE TO RELATED APPLICATION

This non-provisional application claims priority under 35 U.S.C. § 119(a) on Patent Application No. 2018-200797 filed in Japan on Oct. 25, 2018, the entire contents of which are hereby incorporated by reference.

TECHNICAL FIELD

This invention relates to an onium salt, a negative resist composition, and a resist pattern forming process using the same.

BACKGROUND ART

To meet the recent demand for higher integration in integrated circuits, pattern formation to a finer feature size is required. Acid-catalyzed chemically amplified resist compositions are most often used in forming resist patterns with a feature size of 0.2 m or less. High-energy radiation such as UV, deep-UV or EB is used as the light source for exposure of these resist compositions. In particular, while EB lithography is utilized as the ultra-fine microfabrication technique, it is also indispensable in processing a photomask blank to form a photomask for use in semiconductor device fabrication.

Polymers comprising a major proportion of aromatic structure having an acidic side chain, for example, polyhydroxystyrene are useful in resist materials for the KrF excimer laser lithography. These polymers are not used in resist materials for the ArF excimer laser lithography since they exhibit strong absorption at a wavelength of around 200 nm. These polymers, however, are expected to form useful resist materials for the EB and EUV lithography for forming patterns of finer size than the processing limit of ArF excimer laser because they offer high etching resistance.

Resist compositions for photolithography include positive ones in which exposed areas are dissolved away and negative ones in which exposed areas are left as a pattern. A viable composition is selected among them depending on the desired resist pattern. In general, the chemically amplified negative resist composition comprises a polymer which is normally soluble in an aqueous alkaline developer, an acid generator which is decomposed to generate an acid upon exposure to light, and a crosslinker which causes the polymer to crosslink in the presence of the acid serving as a catalyst, thus rendering the polymer insoluble in the developer (sometimes, the crosslinker is incorporated in the polymer). Typically a quencher is added for controlling the diffusion of the acid generated upon light exposure.

Typical of the alkali-soluble units to constitute polymers which dissolve in aqueous alkaline developer are units derived from phenols. A number of negative resist compositions of such type were developed, especially as adapted for exposure to KrF excimer laser light. These compositions have not been used in the ArF excimer laser lithography because the phenolic units are not transmissive to exposure light having a wavelength of 150 to 220 nm. Recently, these compositions are recognized attractive again as the negative resist composition for the short wavelength (e.g., EB or EUV) lithography capable of forming finer size patterns. Exemplary compositions are described in Patent Documents 1 to 3.

Improvements were made in the control of resist sensitivity and pattern profile by properly selecting and combining components used in resist compositions and adjusting processing conditions. One outstanding problem is the diffusion of acid that has a significant impact on the resolution of a chemically amplified resist composition.

A quencher is, in fact, essential for controlling acid diffusion and improving the performance, especially resolution of a resist composition. Studies have been made on the quencher while amines and weak acid onium salts have been generally used. The weak acid onium salts are exemplified in several patent documents. Patent Document 4 describes that the addition of triphenylsulfonium acetate ensures to form a satisfactory resist pattern without T-top profile, a difference in line width between isolated and grouped patterns, and standing waves. Patent Document 5 describes improvements in sensitivity, resolution and exposure margin by the addition of sulfonic acid ammonium salts or carboxylic acid ammonium salts. Also, Patent Document 6 describes that a resist composition for KrF or EB lithography comprising a PAG capable of generating a fluorinated carboxylic acid is improved in resolution and process latitude such as exposure margin and depth of focus. Further, Patent Document 7 describes that a resist composition for $F_2$ laser lithography comprising a PAG capable of generating a fluorinated carboxylic acid is improved in line edge roughness (LER) and solves the footing problem. Patent Documents 4 to 7 refer to the KrF, EB and $F_2$ lithography.

Patent Document 8 describes a positive photosensitive composition for ArF excimer laser lithography comprising a carboxylic acid onium salt. These systems are based on the mechanism that a salt exchange occurs between a weak acid onium salt and a strong acid (sulfonic acid) generated by a PAG upon exposure, to form a weak acid and a strong acid onium salt. That is, the strong acid (sulfonic acid) having high acidity is replaced by a weak acid (carboxylic acid), thereby suppressing acid-catalyzed decomposition reaction of acid labile group and reducing or controlling the distance of acid diffusion. The onium salt apparently functions as a quencher.

However, when a resist composition comprising the foregoing carboxylic acid onium salt or fluorocarboxylic acid onium salt is used in patterning, LER still remains as an outstanding problem. It would be desirable to have a quencher capable of minimizing LER.

CITATION LIST

Patent Document 1: JP-A 2006-201532 (US 20060166133, EP 1684118)
Patent Document 2: JP-A 2006-215180
Patent Document 3: JP-A 2008-249762 (U.S. Pat. No. 9,075,306, EP 1975711)
Patent Document 4: JP 3955384 (U.S. Pat. No. 6,479,210)
Patent Document 5: JP-A H11-327143
Patent Document 6: JP 4231622 (U.S. Pat. No. 6,485,883)
Patent Document 7: JP 4116340 (U.S. Pat. No. 7,214,467)
Patent Document 8: JP 4226803 (U.S. Pat. No. 6,492,091)
Patent Document 9: JP-A 2001-330947 (U.S. Pat. No. 6,605,409, EP 1158363)

DISCLOSURE OF INVENTION

An object of the invention is to provide a compound useful as a quencher, a negative resist composition comprising the compound, which is processed by lithography to form a resist pattern with improved resolution and minimal LER, and a pattern forming process using the resist composition.

The inventors have found that a resist composition comprising an onium salt of benzenesulfonimide having a bulky substituent group or sulfonimide having an alicyclic structure as a quencher can be processed by lithography to form a resist pattern with minimal LER.

In one aspect, the invention provides an onium salt having the formula (A).

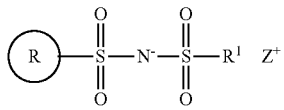
(A)

Herein $R^1$ is a $C_1$-$C_{20}$ monovalent hydrocarbon group which may contain a heteroatom; the ring R is a group having the formula (A1), or a $C_6$-$C_{30}$ group having an alicyclic structure in which some carbon may be replaced by a moiety containing sulfur, oxygen or nitrogen,

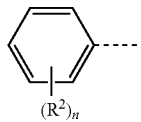
(A1)

wherein the broken line designates a valence bond, $R^2$ is each independently a $C_1$-$C_{20}$ monovalent hydrocarbon group which may contain a heteroatom, n is an integer of 2 to 5; $Z^+$ is a sulfonium cation having the formula (A2) or iodonium cation having the formula (A3):

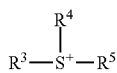
(A2)

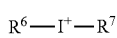
(A3)

wherein $R^3$ to $R^7$ are each independently a $C_1$-$C_{20}$ monovalent hydrocarbon group which may contain a heteroatom, any two or more of $R^3$, $R^4$ and $R^5$ may bond together to form a ring with the sulfur atom to which they are attached.

Preferably, the ring R is a group having the formula (A1). More preferably, $R^2$ is a $C_3$-$C_{20}$ branched or cyclic monovalent hydrocarbon group.

Preferably, at least one $R^2$ is bonded at the ortho-position relative to the carbon atom bonded to the sulfonyl group.

Preferably, n is an integer of 3 to 5.

In a second aspect, the invention provides a negative resist composition comprising (A) the onium salt defined above, and (B) a base polymer containing a polymer comprising recurring units having the formula (B1).

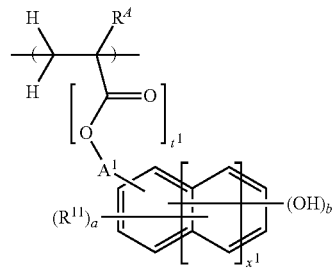
(B1)

Herein $R^A$ is hydrogen, fluorine, methyl or trifluoromethyl, $R^{11}$ is each independently halogen, an optionally halogenated $C_2$-$C_8$ acyloxy group, optionally halogenated $C_1$-$C_6$ alkyl group, or optionally halogenated $C_1$-$C_6$ alkoxy group, $A^1$ is a single bond or $C_1$-$C_{10}$ alkanediyl group in which an ether bond may intervene in a carbon-carbon bond, $t^1$ is 0 or 1, $x^1$ is an integer of 0 to 2, a is an integer satisfying $0 \leq a \leq 5+2x^1-b$, and b is an integer of 1 to 5.

In a preferred embodiment, the polymer further comprises recurring units of at least one type selected from recurring units having the formulae (B2), (B3) and (B4).

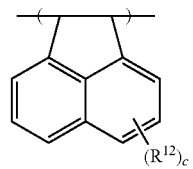
(B2)

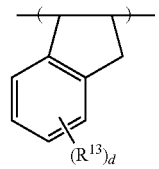
(B3)

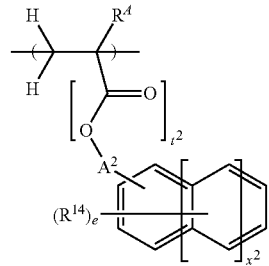
(B4)

Herein $R^A$ is hydrogen, fluorine, methyl or trifluoromethyl; $R^{12}$ and $R^{13}$ are each independently hydroxyl, halogen, acetoxy, an optionally halogenated $C_1$-$C_8$ alkyl group, optionally halogenated $C_1$-$C_8$ primary alkoxy group, $C_2$-$C_8$ secondary alkoxy group, optionally halogenated $C_2$-$C_8$ acyloxy group, or optionally halogenated $C_2$-$C_8$ alkylcarbonyloxy group; $R^{14}$ is an acetyl group, acetoxy group, $C_1$-$C_{20}$ alkyl group, $C_1$-$C_{20}$ primary alkoxy group, $C_2$-$C_{20}$ secondary alkoxy group, $C_2$-$C_{20}$ acyloxy group, $C_2$-$C_{20}$ alkoxyalkyl group, $C_2$-$C_{20}$ alkylthioalkyl group, halogen atom, nitro group, or cyano group; $A^2$ is a single bond or $C_1$-$C_{10}$ alkanediyl group in which an ether bond may intervene in a carbon-carbon bond; c and d are each independently an integer of 0 to 4, e is an integer of 0 to 5, $x^2$ is an integer of 0 to 2, and $t^2$ is 0 or 1.

In a preferred embodiment, the polymer further comprises recurring units having the formula (B5).

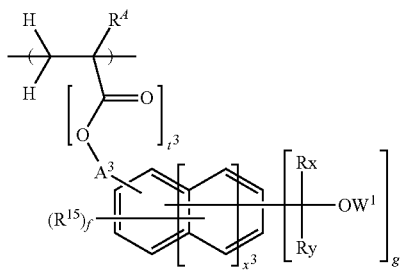
(B5)

Herein $R^A$ is hydrogen, fluorine, methyl or trifluoromethyl; $R^{15}$ is each independently halogen, an optionally halogenated $C_2$-$C_8$ acyloxy group, optionally halogenated $C_1$-$C_6$ alkyl group, or optionally halogenated $C_1$-$C_6$ alkoxy group; $A^3$ is a single bond or $C_1$-$C_{10}$ alkanediyl group in which an ether bond may intervene in a carbon-carbon bond; $W^1$ is hydrogen, a $C_1$-$C_{10}$ monovalent aliphatic hydrocarbon group in which an ether bond, carbonyl moiety or carbonyloxy moiety may intervene in a carbon-carbon bond, or an optionally substituted monovalent aromatic ring group; Rx and Ry are each independently hydrogen, an optionally hydroxy or alkoxy-substituted $C_1$-$C_{15}$ alkyl group or an optionally substituted monovalent aromatic ring group, with the proviso that both Rx and Ry are not hydrogen at the same time, Rx and Ry may bond together to form a ring with the carbon atom to which they are attached; $x^3$ is an integer of 0 to 2, $t^3$ is 0 or 1, f is an integer satisfying $0 \le f \le 5+2x^3-g$, and g is an integer of 1 to 3.

In a preferred embodiment, the polymer further comprises recurring units of at least one type selected from recurring units having the formulae (B6), (B7) and (B8).

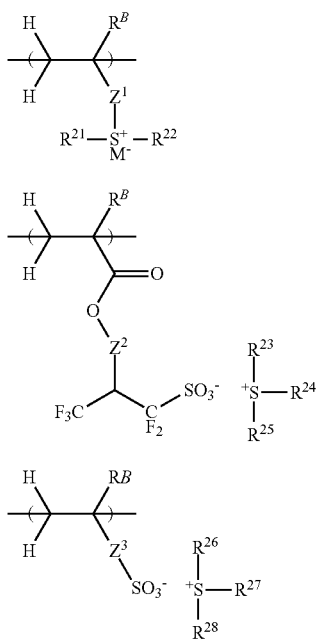

Herein $R^B$ is each independently hydrogen or methyl; $Z^1$ is a single bond, phenylene group, —O—$Z^{11}$—, —C(=O)—O—$Z^{11}$—, or —C(=O)—NH—$Z^{11}$—, $Z^{11}$ is a $C_2$-$C_6$ alkanediyl, $C_2$-$C_6$ alkenediyl or phenylene group, which may contain a carbonyl moiety, ester bond, ether bond or hydroxyl moiety; $Z^2$ is a single bond or —$Z^{21}$—C(=O)—O—, $Z^{21}$ is a $C_1$-$C_{20}$ divalent hydrocarbon group which may contain a heteroatom: $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ alkanediyl, $C_2$-$C_6$ alkenediyl or phenylene group, which may contain a carbonyl moiety, ester bond, ether bond or hydroxyl moiety; $R^{21}$ to $R^{28}$ are each independently a $C_1$-$C_{20}$ monovalent hydrocarbon group which may contain a heteroatom, or $R^{21}$ and $R^{22}$ may bond together to form a ring with the sulfur atom to which they are attached, or any two or more of $R^{23}$, $R^{24}$ and $R^{25}$ may bond together to form a ring with the sulfur atom to which they are attached, any two or more of $R^{26}$, $R^{27}$ and $R^{28}$ may bond together to form a ring with the sulfur atom to which they are attached; and $M^-$ is a non-nucleophilic counter ion.

In a preferred embodiment, the polymer comprises recurring units having the formula (B1-1), recurring units having the formula (B5-1), and recurring units having the formula (B7).

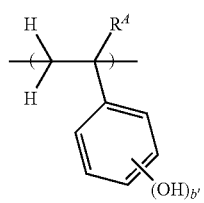
(B1-1)

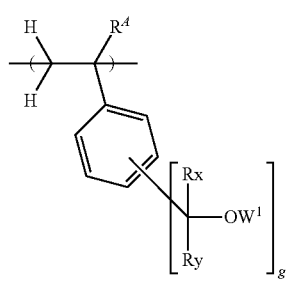
(B5-1)

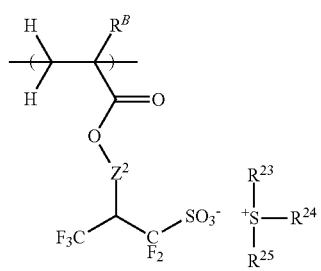
(B7)

Herein $R^A$ is each independently hydrogen, fluorine, methyl or trifluoromethyl; $R^B$ is hydrogen or methyl; $W^1$ is hydrogen, a $C_1$-$C_{10}$ monovalent aliphatic hydrocarbon group in which an ether bond, carbonyl moiety or carbonyloxy moiety may intervene in a carbon-carbon bond, or an optionally substituted monovalent aromatic ring group; Rx and Ry are each independently hydrogen, an optionally hydroxy or alkoxy-substituted $C_1$-$C_{15}$ alkyl group or an optionally substituted monovalent aromatic ring group, with the proviso that both Rx and Ry are not hydrogen at the same time, Rx and Ry may bond together to form a ring with the carbon atom to which they are attached; $Z^2$ is a single bond or —$Z^{21}$—C(=O)—O—, $Z^{21}$ is a $C_1$-$C_{20}$ divalent hydrocarbon group which may contain a heteroatom; $R^{23}$ to $R^{25}$ are each independently a $C_1$-$C_{20}$ monovalent hydrocarbon group which may contain a heteroatom, or any two or more of $R^{23}$, $R^{24}$ and $R^{25}$ may bond together to form a ring with the sulfur atom to which they are attached; b' is an integer of 1 to 3, and g is an integer of 1 to 3.

In a preferred embodiment, the base polymer (B) further contains a polymer free of recurring units having the formula (B6), recurring units having the formula (B7), and recurring units having the formula (B8).

The negative resist composition may further comprise (C) a crosslinker.

In another embodiment, the negative resist composition is free of a crosslinker.

The negative resist composition may further comprise (E) an acid generator.

In a further aspect, the invention provides a photomask blank coated with the negative resist composition defined above.

In a still further aspect, the invention provides a resist pattern forming process comprising the steps of applying the negative resist composition defined above onto a substrate to form a resist film thereon, exposing the resist film patternwise to high-energy radiation, and developing the resist film in an alkaline developer to form a resist pattern.

Preferably, the high-energy radiation is EUV or EB.

In one embodiment, the substrate is a photomask blank.

Advantageous Effects of Invention

Owing to the onium salt, the negative resist composition of the invention is effective for controlling acid diffusion during the exposure step. When the composition is coated as a resist film and processed to form a pattern, the resist film exhibits a very high resolution during pattern formation, and forms a pattern with minimal LER. The pattern forming process using the negative resist composition can form a resist pattern with minimal LER while maintaining a high resolution. The invention is best suited for a micropatterning process, typically EUV or EB lithography.

DESCRIPTION OF EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, Me stands for methyl, Ac stands for acetyl, and the broken line designates a valence bond.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LER: line edge roughness It is understood that for some structures represented by chemical formulae, there can exist enantiomers and diastereomers because of the presence of asymmetric carbon atoms. In such a case, a single formula collectively represents all such isomers. The isomers may be used alone or in admixture.

Onium Salt

One embodiment of the invention is an onium salt having the formula (A).

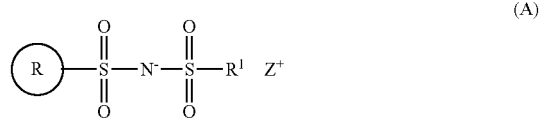

In formula (A), $R^1$ is a $C_1$-$C_{20}$ monovalent hydrocarbon group which may contain a heteroatom. The monovalent hydrocarbon group may be straight, branched or cyclic. In the hydrocarbon group, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl moiety, cyano moiety, carbonyl moiety, ether bond, thioether bond, ester bond, sulfonic acid ester bond, carbonate bond, carbamate bond, lactone ring, sultone ring, carboxylic anhydride (—C(=O)—O—C(=O)—) or haloalkyl moiety.

Examples of the $C_1$-$C_{20}$ monovalent hydrocarbon group which may contain a heteroatom include $C_1$-$C_{20}$ straight or branched alkyl groups such as methyl, ethyl, propyl, isopropyl, n-butyl, sec-butyl, tert-butyl, n-pentyl, tert-pentyl, n-hexyl, n-octyl, n-nonyl, n-decyl, $C_1$-$C_{20}$ monovalent saturated cyclic hydrocarbon groups such as cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl, $C_6$-$C_{10}$ aryl groups such as phenyl, naphthyl, and anthracenyl, and halo-substituted alkyl groups such as fluoromethyl, difluoromethyl, trifluoromethyl, 2,2,2-trifluoroethyl, 1,1,2,2,2-pentafluoroethyl, and 1,1,1,3,3,3-hexafluoroethyl.

The ring R is a group having the formula (A1), or a $C_6$-$C_{30}$ group having an alicyclic structure in which some carbon may be replaced by a moiety containing sulfur, oxygen or nitrogen.

In formula (A1), the broken line designates a valence bond. $R^2$ is each independently a $C_1$-$C_{20}$ monovalent hydrocarbon group which may contain a heteroatom. The monovalent hydrocarbon group may be straight, branched or cyclic. In the hydrocarbon group, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl moiety, cyano moiety, carbonyl moiety, ether bond, thioether bond, ester bond, sulfonic acid ester bond, carbonate bond, carbamate bond, lactone ring, sultone ring, carboxylic anhydride (—C(=O)—O—C(=O)—) or haloalkyl moiety.

Examples of the $C_1$-$C_{20}$ monovalent hydrocarbon group which may contain a heteroatom, represented by $R^2$, include $C_1$-$C_{20}$ straight or branched alkyl groups such as methyl, ethyl, propyl, isopropyl, n-butyl, sec-butyl, tert-butyl, n-pentyl, tert-pentyl, n-hexyl, n-octyl, n-nonyl, n-decyl, $C_1$-$C_{20}$ monovalent saturated cyclic hydrocarbon groups such as cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl, and $C_6$-$C_0$ aryl groups such as phenyl, naphthyl, and anthracenyl.

Of these, $R^2$ is preferably a $C_3$-$C_{20}$ branched or cyclic monovalent hydrocarbon group. This configuration ensures that the sulfonimide acid generated after neutralization has a fully bulky structure. Accordingly, when the sulfonimide acid generated after neutralization contributes slightly to insolubilization, its reactivity is suppressed, contributing to an improvement in LER.

In formula (A1), preferably at least one $R^2$ is bonded at the ortho-position relative to the carbon atom bonded to the sulfonyl group. With this configuration, the active site on the sulfonimide acid generated after neutralization is sterically blocked by the substituent group at ortho-position whereby reactivity is suppressed. Accordingly, when the sulfonimide acid generated after neutralization contributes slightly to insolubilization, reactivity is suppressed, contributing to an improvement in LER.

In formula (A1), n is an integer of 2 to 5, preferably 3 to 5.

Examples of the $C_6$-$C_{30}$ group having an alicyclic structure, represented by the ring R, are shown below, but not limited thereto.

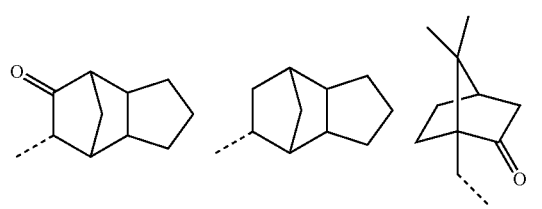

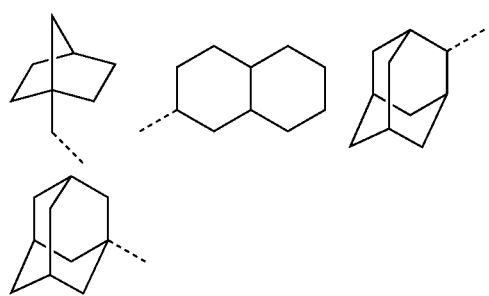

In formula (A), $Z^+$ is a sulfonium cation having the formula (A2) or an iodonium cation having the formula (A3).

In formulae (A2) and (A3), $R^3$ to $R^7$ are each independently a $C_1$-$C_{20}$ monovalent hydrocarbon group which may contain a heteroatom, any two or more of $R^3$, $R^4$ and $R^5$ may bond together to form a ring with the sulfur atom to which they are attached.

The $C_1$-$C_{20}$ monovalent hydrocarbon group which may contain a heteroatom, represented by $R^3$ to $R^7$, may be straight, branched or cyclic. Specific examples thereof are as exemplified above for $R^1$ in formula (A).

When any two or more of $R^3$, $R^4$ and $R^5$ in formula (A2) bond together to form a ring with the sulfur atom to which they are attached, examples of the ring are shown below, but not limited thereto.

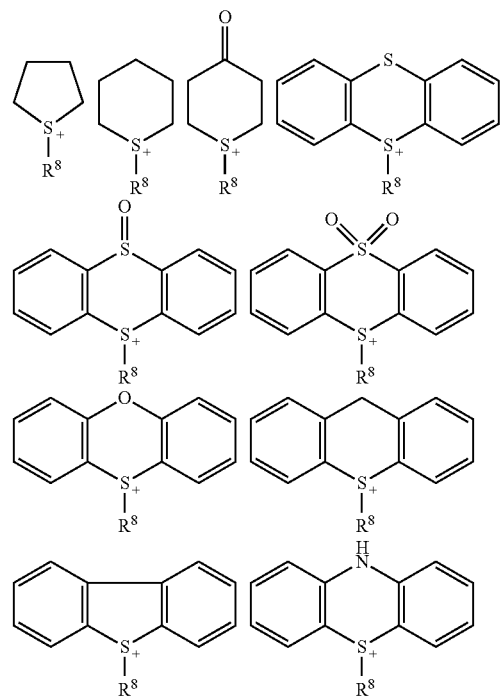

In the above formulae, $R^8$ is a $C_1$-$C_{20}$ monovalent hydrocarbon group which may contain a heteroatom, examples of which are as exemplified above for $R^1$ in formula (A).

Examples of the sulfonium cation having formula (A2) are given below, but not limited thereto.

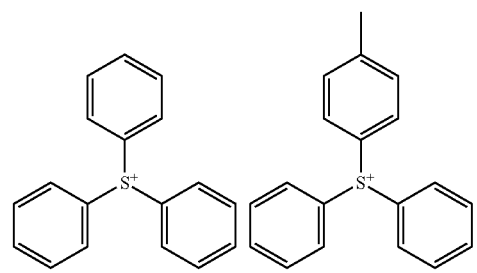

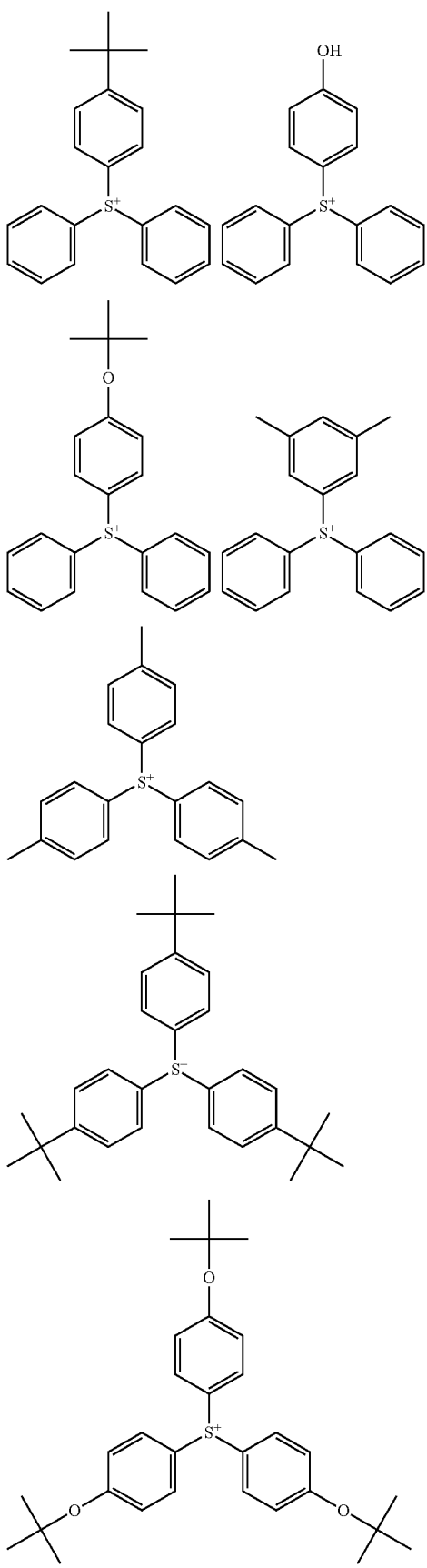
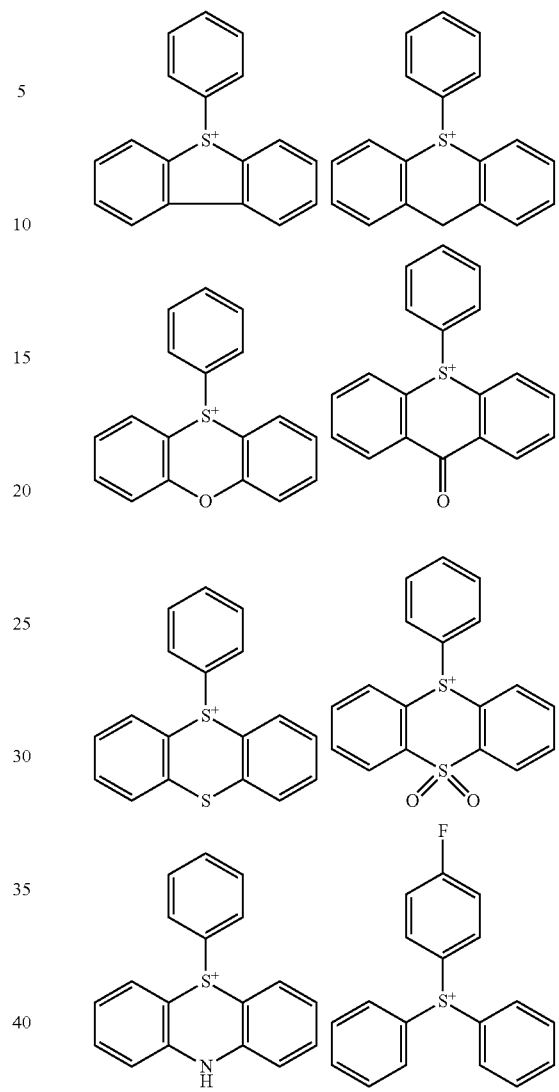

In formula (A3), the $C_1$-$C_{20}$ monovalent hydrocarbon group which may contain a heteroatom, represented by $R^6$ and $R^7$, is preferably an aryl group.

Preferred examples of the iodonium cation having formula (A3) include bis(4-methylphenyl)iodonium, bis(4-ethylphenyl)iodonium, bis(4-tert-butylphenyl)iodonium, bis[4-(1,1-dimethylpropyl)phenyl]iodonium, 4-methoxyphenylphenyliodonium, 4-tert-butoxyphenylphenyliodonium, 4-acryloyloxyphenylphenyliodonium, and 4-methacryloyloxyphenylphenyliodonium, with bis(4-tert-butylphenyl)iodonium being most preferred.

Examples of the anion in the onium salt having formula (A) are given below, but not limited thereto.

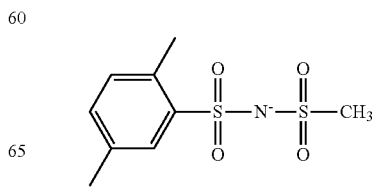

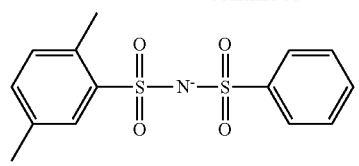
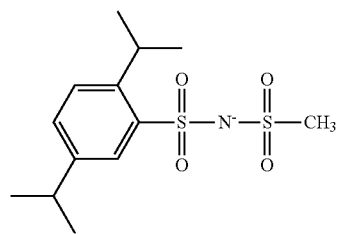
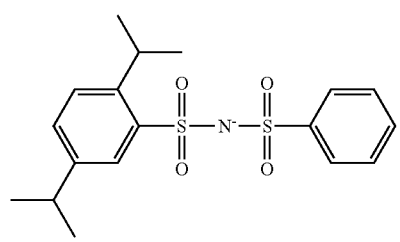
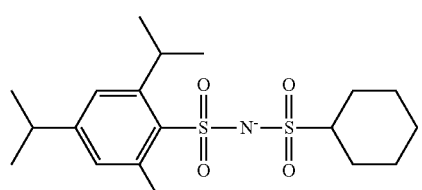
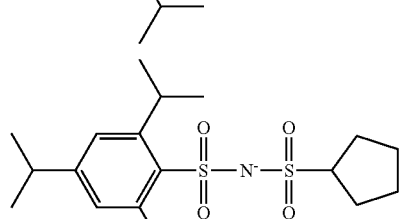
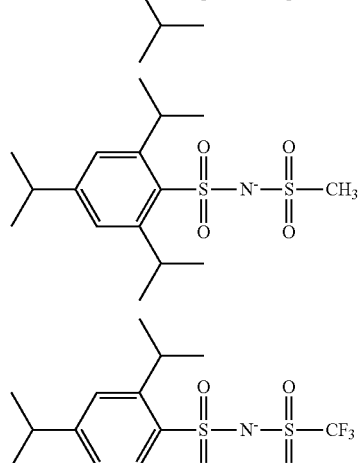
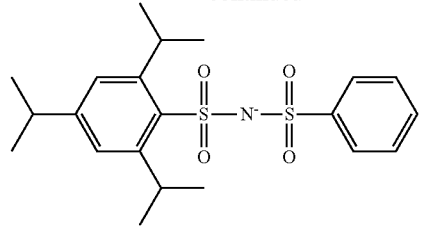
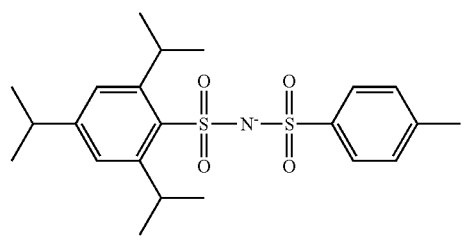
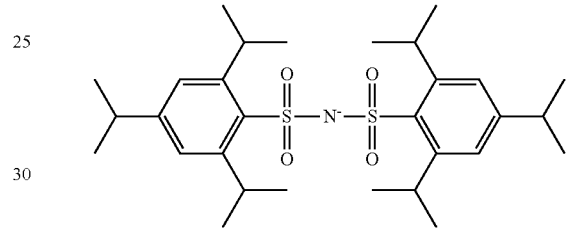
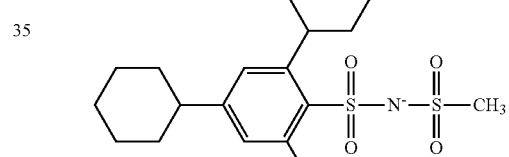
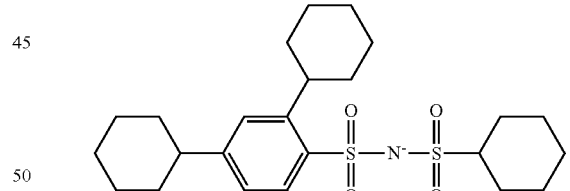
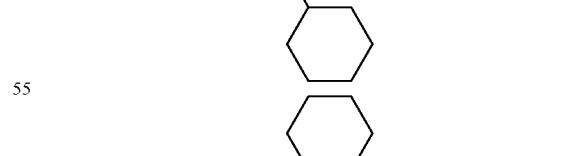
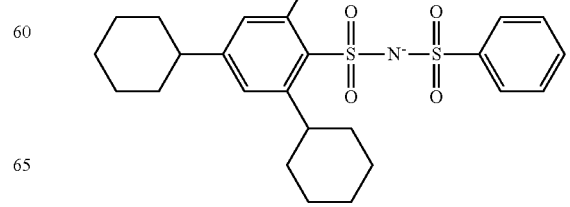

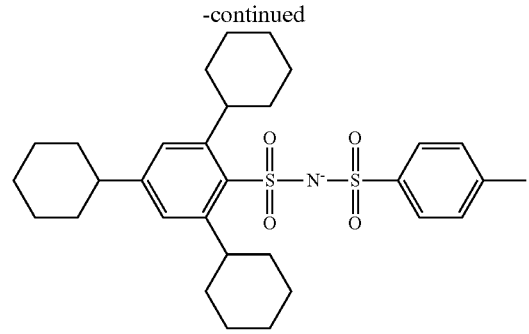
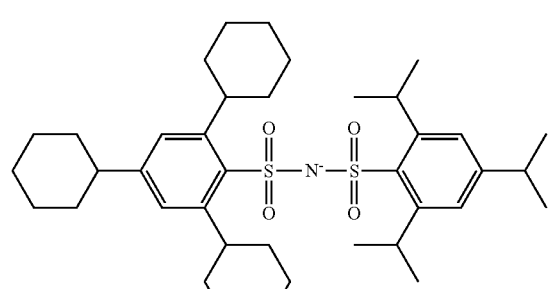
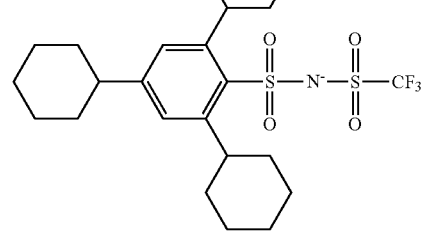
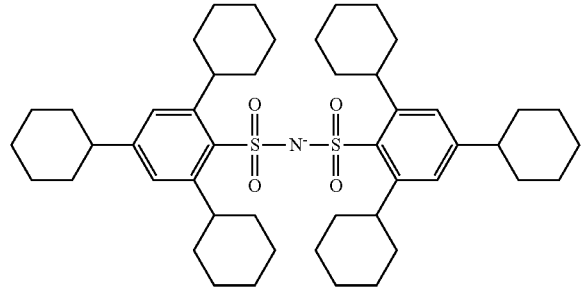
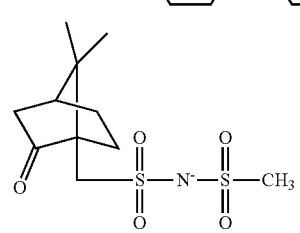
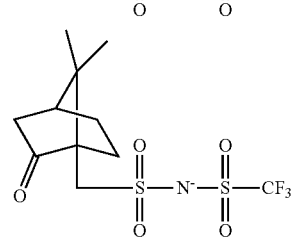
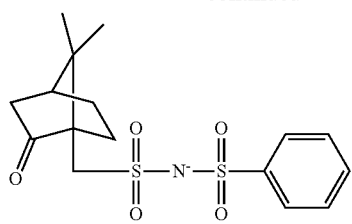
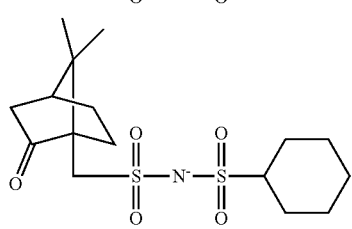
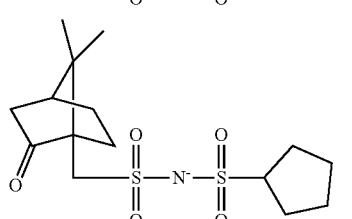
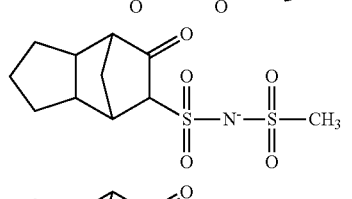
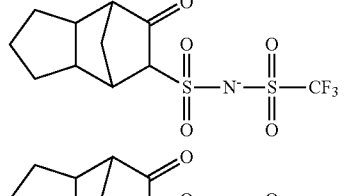
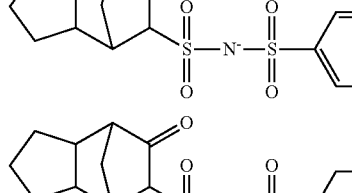
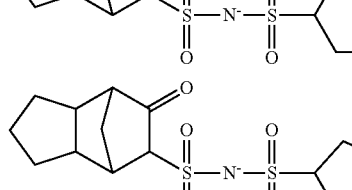
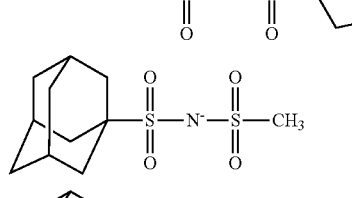
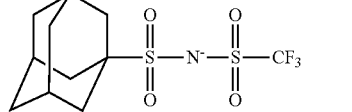

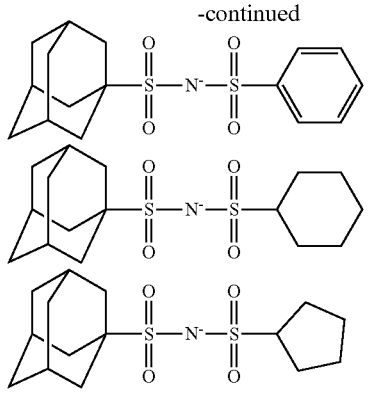

Exemplary structures for the onium salt include arbitrary combinations of anions with cations, both as exemplified above.

The onium salt having formula (A) may be synthesized by a combination of well-known organic chemistry methods, for example, according to the scheme shown below.

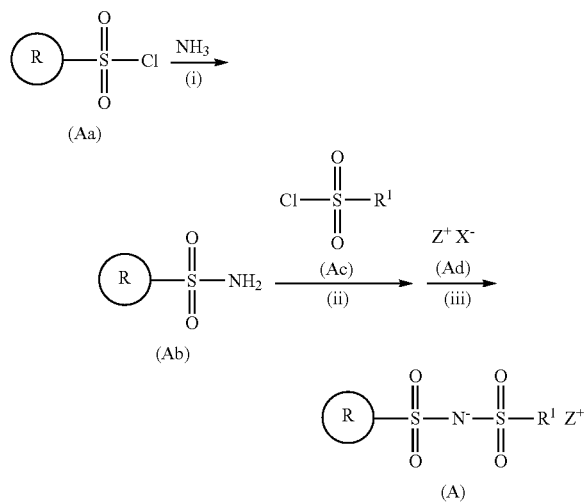

Herein ring R, $R^1$, and $Z^+$ are as defined above, and $X^-$ is a halide ion.

First, in step (i), a sulfonyl chloride compound (Aa) is reacted with ammonia to synthesize a sulfonamide compound (Ab). The reaction may be carried out, for example, by dissolving sulfonyl chloride compound (Aa) in a solvent, adding ammonia water thereto or blowing ammonia gas therein, and optionally heating or cooling the solution.

Examples of the solvent which can be used in the reaction of step (i) include water, ethers such as tetrahydrofuran (THF), diethyl ether, diisopropyl ether, di-n-butyl ether, and 1,4-dioxane, hydrocarbons such as n-hexane, n-heptane, benzene, toluene, and xylene, aprotic polar solvents such as acetonitrile, dimethyl sulfoxide (DMSO), N,N-dimethylformamide (DMF), chlorinated organic solvents such as methylene chloride, chloroform and carbon tetrachloride. Any suitable one may be chosen from these solvents, depending on reaction conditions, while the solvents may be used alone or in admixture.

The amount of ammonia used is preferably 1 to 30 moles, more preferably 1 to 5 moles per mole of sulfonyl chloride compound (Aa).

In step (i), the reaction temperature is preferably −20° C. to 80° C., more preferably 0 to 40° C., and the reaction time is preferably 5 minutes to 24 hours, more preferably 1 to 20 hours.

Next, in step (ii), sulfonamide compound (Ab) is reacted with a sulfonyl chloride compound (Ac). Examples of the solvent which can be used in step (ii) include ethers such as THF, diethyl ether, diisopropyl ether, di-n-butyl ether, and 1,4-dioxane, hydrocarbons such as n-hexane, n-heptane, benzene, toluene, and xylene, aprotic polar solvents such as acetonitrile, DMSO, DMF, and chlorinated organic solvents such as methylene chloride, chloroform and carbon tetrachloride. Any suitable one may be chosen from these solvents, depending on reaction conditions, while the solvents may be used alone or in admixture.

For promoting the reaction, there may be co-present a base such as pyridine, triethylamine, 2,6-lutidine, or collidine. For promoting the reaction, it is also preferred to add 4-dimethylaminopyridine (DMAP).

The amount of sulfonyl chloride compound (Ac) used is preferably 1 to 30 moles, more preferably 1 to 5 moles per mole of sulfonamide compound (Ab).

In step (ii), the reaction temperature is preferably −20° C. to 80° C., more preferably 0 to 40° C., and the reaction time is preferably 5 minutes to 24 hours, more preferably 1 to 20 hours.

Finally, in step (iii), ion exchange reaction is carried out between the reaction product of step (ii) and an onium salt (Ad) to synthesize the desired onium salt (A).

Negative Resist Composition

Another embodiment of the invention is a negative resist composition comprising (A) the onium salt defined above and (B) a base polymer.

The onium salt functions as a quencher in the negative resist composition. The quencher function mechanism is considered as follows. The acid generated by an acid generator in the resist composition in the exposed region should have a strong acidity enough to render the base polymer alkali insoluble. For example, α-fluorinated sulfonic acid, imide acid (or imidic acid) and methide acid are used in the ArF lithography. In a resist composition system where the acid generator and the inventive onium compound co-exist, the acid generated by the acid generator undergoes ion exchange with the inventive onium salt to convert to a sulfonium or iodonium salt again and instead, the anion of the inventive onium salt is released as carboxylic acid. Differently stated, by ion exchange, the strong acid generated by the acid generator is neutralized with the inventive onium salt. That is, the inventive onium salt functions as a quencher. Another mechanism that the cation of the inventive sulfonimide salt is photo-decomposed to generate sulfonimide acid is contemplated. However, the sulfonimide acid is a weak acid, which contributes little to the reaction to render the base polymer alkali insoluble.

The onium salt type quencher tends to form a resist pattern with a reduced LER as compared with the conventional quenchers in the form of amine compounds. This is presumably because salt exchange between strong acid and the inventive onium salt type quencher is infinitely repeated. The site where strong acid is generated at the end of exposure shifts from the site where the onium salt of strong acid generation type is initially present. It is believed that since the cycle of photo-acid generation and salt exchange is repeated many times, the acid generation point is averaged, and this smoothing effect acts to reduce the LER of a resist pattern after development.

It is also believed that the inventive quencher is, of course, present in the unexposed region as well. The quencher traps the acid that has diffused thereto from the exposed region via ion exchange reaction. This ensures to quench the acid that has diffused to the unexposed region. Then the contrast between exposed and unexposed regions is enhanced, leading to substantial improvements in resolution and LER.

As the compound that exerts a quencher effect via the same mechanism, Patent Documents 5 and 8 report the use of carboxylic acid onium salts, alkanesulfonic acid onium salts, and arenesulfonic acid onium salts as the quencher. On use of an alkanesulfonic acid onium salt or arenesulfonic acid onium salt, the generated acid has such an acid strength that part thereof in the overexposed region may induce alkali-insolubilizing reaction of the base polymer rather than the quencher, leading to an increase of acid diffusion, which invite degradation of resist performance factors like resolution and LER.

Also in the case of alkanecarboxylic acid onium salt, the carboxylic acid generated therefrom has a weak acidity and is substantially ineffective for rendering the base polymer alkali insoluble. However, the strong acid (from the acid generator) that has diffused to the unexposed region is not completely trapped, with the values of resolution and LER being unsatisfactory. In contrast, the inventive quencher has a satisfactory quenching ability and more effectively traps the acid that has diffused to the unexposed region than the alkanecarboxylic acid onium salt.

Patent Document 9 describes a bis(p-toluenesulfonyl) imide salt. Since this compound is inferior in bulkiness to the inventive onium salt, its acid diffusion controlling ability is unsatisfactory as compared with the inventive onium salt.

Since the inventive onium salt is a salt compound, it is effective for preventing chemical flare by acid upon EB writing and does not volatilize by local heat during high current EB writing. Accordingly, it exerts the quencher function in the written region. Also, since the onium salt is retained in the non-written region without volatilization, it prevents unnecessary negative toning and is effective for reducing defects.

An appropriate amount of the onium salt (A) is 0.1 to 50 parts, more preferably 0.5 to 30 parts by weight per 100 parts by weight of the base polymer (B). As long as its amount is in the range, the onium salt fully functions as a quencher, eliminating any performance problems such as sensitivity drop, solubility shortage, and foreign particles. The onium salt (A) may be used alone or in admixture of two or more.

(B) Base Polymer

The negative resist composition also comprises (B) a base polymer containing a polymer comprising recurring units having the formula (B1). It is noted that the recurring unit having formula (B1) is simply referred to as recurring unit (B1), and the polymer is referred to as polymer (B). The recurring units (B1) are effective for imparting etching resistance, adhesion to substrates, and solubility in alkaline developer.

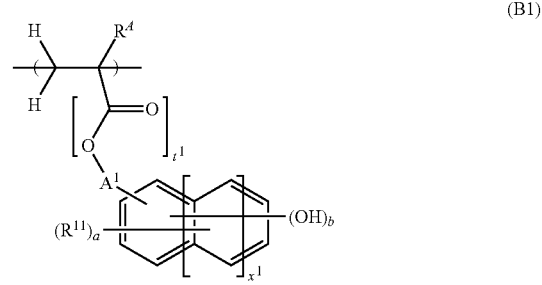

In formula (B1), $R^A$ is hydrogen, fluorine, methyl or trifluoromethyl, with hydrogen or methyl being preferred. $R^{11}$ is each independently halogen, an optionally halogenated $C_2$-$C_5$ acyloxy group, optionally halogenated $C_1$-$C_6$ alkyl group, or optionally halogenated $C_1$-$C_6$ alkoxy group. $A^1$ is a single bond or a $C_1$-$C_{10}$ alkanediyl group in which an ether bond may intervene in a carbon-carbon bond, $t^1$ is 0 or 1, $x^1$ is an integer of 0 to 2, a is an integer satisfying $0 \leq a \leq 5+2x^1-b$, and b is an integer of 1 to 5.

Examples of the alkanediyl group represented by $A^1$ include methylene, ethylene, propylene, butylene, pentylene, hexylene, and structural isomers of a carbon skeleton having branched or cyclic structure. For the alkanediyl group containing an ether bond, in case $t^1=1$ in formula (B1), the ether bond may be incorporated at any position excluding the position between the α- and β-carbons relative to the ester oxygen. In case $t^1=0$, the atom in $A^1$ that bonds with the main chain becomes an ethereal oxygen atom, and a second ether bond may be incorporated at any position excluding the position between the α- and β-carbons relative to that ether bond. Alkanediyl groups having no more than 10 carbon atoms are desirable because of a sufficient solubility in alkaline developer.

Preferred examples of the hydrocarbon portion in the acyloxy, alkyl and alkoxy groups represented by $R^{11}$ include methyl, ethyl, propyl, isopropyl, butyl, pentyl, hexyl and structural isomers of a carbon skeleton having branched or cyclic structure. As long as the carbon count is within the upper limit, good solubility in alkaline developer is available.

In formula (B1), $x^1$ is an integer of 0 to 2. The corresponding structure represents a benzene skeleton when $x^1=0$, a naphthalene skeleton when $x^1=1$, and an anthracene skeleton when $x^1=2$. The subscript a is an integer in the range: $0 \leq a \leq 5+2x^1-b$. In case $x^1=0$, preferably a is an integer of 0 to 3, and b is an integer of 1 to 3. In case x=1 or 2, preferably a is an integer of 0 to 4, and b is an integer of 1 to 3.

Preferred examples of the recurring units (B1) wherein $t^1=0$ and $A^1$ is a single bond (meaning that the aromatic ring is directly bonded to the main chain of the polymer), that is, recurring units free of a linker (—CO—O-$A^1$-) include units derived from 3-hydroxystyrene, 4-hydroxystyrene, 5-hydroxy-2-vinylnaphthalene, and 6-hydroxy-2-vinylnaphthalene. More preferred are recurring units represented by the following formula (B1-1).

(B1-1)

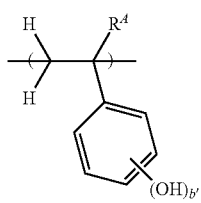

Herein $R^A$ is as defined above and b' is an integer of 1 to 3.

Preferred examples of the recurring units (B1) wherein $t^1=1$, that is, having a linker (—CO—O—$A^1$-) are shown below, but not limited thereto. Herein $R^A$ is as defined above.

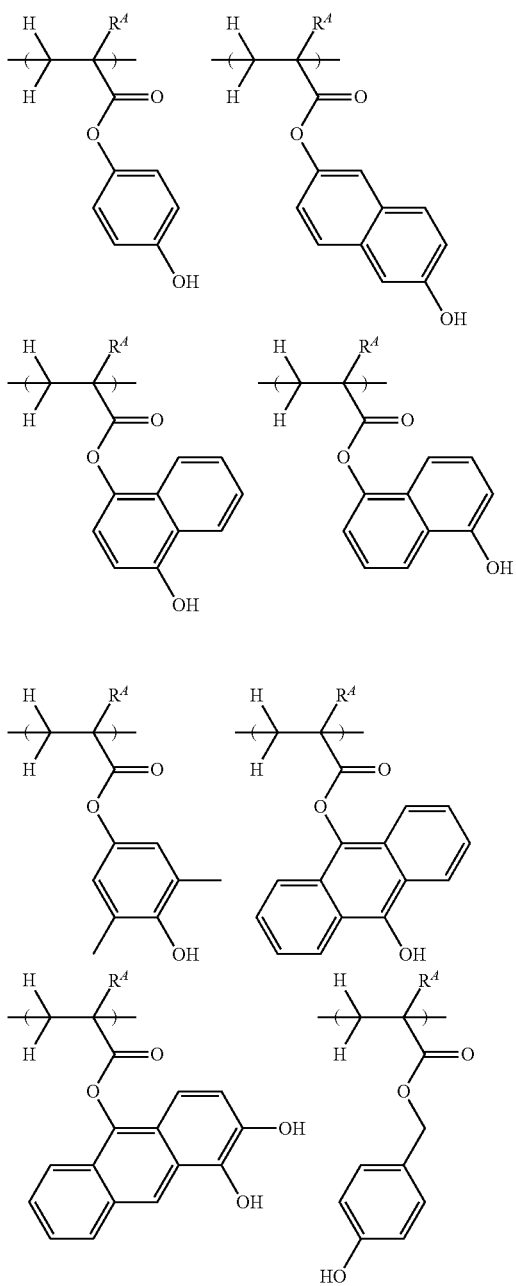

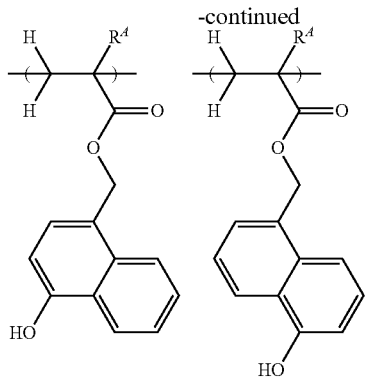

For the purpose of improving etch resistance, preferably the polymer (B) further comprises recurring units of at least one type selected from recurring units having the formula (B2), recurring units having the formula (B3) and recurring units having the formula (B4). Notably these units are simply referred to as recurring units (B2), (B3) and (B4).

(B2)

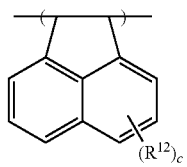

(B3)

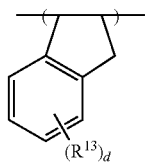

(B4)

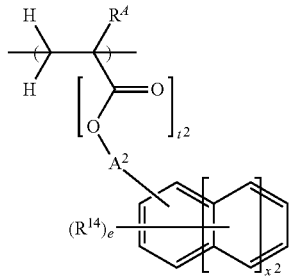

Herein $R^A$ is as defined above. $R^{12}$ and $R^{13}$ are each independently a hydroxyl group, halogen atom, acetoxy group, optionally halogenated $C_1$-$C_8$ alkyl group, optionally halogenated $C_1$-$C_8$ primary alkoxy group, $C_2$-$C_8$ secondary alkoxy group, optionally halogenated $C_2$-$C_8$ acyloxy group, or optionally halogenated $C_2$-$C_8$ alkylcarbonyloxy group. $R^{14}$ is an acetyl group, acetoxy group, $C_1$-$C_{20}$ alkyl group, $C_1$-$C_{20}$ primary alkoxy group, $C_2$-$C_{20}$ secondary alkoxy group, $C_2$-$C_{20}$ acyloxy group, $C_2$-$C_{20}$ alkoxyalkyl group, $C_2$-$C_{20}$ alkylthioalkyl group, halogen atom, nitro group, or cyano group. $A^2$ is a single bond or $C_1$-$C_{10}$ alkanediyl group in which an ether bond may intervene in a carbon-carbon bond, c and d are each independently an integer of 0 to 4, e is an integer of 0 to 5, $x^2$ is an integer of 0 to 2, and $t^2$ is 0 or 1.

Preferred examples of the alkanediyl group represented by $A^2$ include methylene, ethylene, propylene, butylene, pentylene, hexylene and structural isomers of a carbon skeleton having branched or cyclic structure. For the alkanediyl group containing an ether bond, in case $t^2=1$ in formula (B4), the ether bond may be incorporated at any position excluding the position between the α- and β-carbons relative to the ester oxygen. In case $t^2=0$ in formula (B4), the atom in $A^2$ that bonds with the main chain becomes an ethereal oxygen atom, and a second ether bond may be incorporated at any position excluding the position between the α- and β-carbons relative to that ether bond. Alkanediyl groups having no more than 10 carbon atoms are desirable because of a high solubility in alkaline developer.

Preferred examples of the hydrocarbon portion in the alkyl, alkoxy, acyloxy and alkylcarbonyloxy groups represented by $R^{12}$ and $R^{13}$ include methyl, ethyl, propyl, isopropyl, butyl, pentyl, hexyl and structural isomers of a carbon skeleton having branched or cyclic structure. As long as the carbon count is within the upper limit, good solubility in alkaline developer is available.

Preferred examples of the group $R^{14}$ include chlorine, bromine, iodine, methyl, ethyl, propyl, butyl, pentyl, hexyl and structural isomers thereof, cyclopentyl, cyclohexyl, methoxy, ethoxy, propoxy, butoxy, pentyloxy, hexyloxy and structural isomers of its hydrocarbon moiety, cyclopentyloxy, and cyclohexyloxy. Inter alia, methoxy and ethoxy are useful. An acyloxy group may be readily introduced into a polymer even after polymerization, by a chemical modification method and is advantageously utilized for fine adjustment of the solubility of the base polymer in alkaline developer. Preferred acyloxy groups include methylcarbonyloxy, ethylcarbonyloxy, propylcarbonyloxy, butylcarbonyloxy, pentylcarbonyloxy, hexylcarbonyloxy and structural isomers thereof cyclopentylcarbonyloxy, cyclohexylcarbonyloxy, and benzoyloxy. As long as the carbon count is equal to or less than 20, an appropriate effect of controlling or adjusting (typically reducing) the solubility of the polymer in alkaline developer is obtainable, and the generation of scum or development defects may be suppressed. Of the foregoing preferred substituent groups, such substituent groups as chlorine, bromine, iodine, methyl, ethyl and methoxy are useful because corresponding monomers may be readily prepared.

In formula (B4), $x^2$ is an integer of 0 to 2. The corresponding structure represents a benzene skeleton when $x^2=0$, a naphthalene skeleton when $x^2=1$, and an anthracene skeleton when $x^2=2$. In case $x^2=0$, preferably e is an integer of 0 to 3; in case $x^1=1$ or 2, preferably e is an integer of 0 to 4.

Preferred examples of the recurring units (B4) wherein $t^2$ is 0 and $A^2$ is a single bond (meaning that the aromatic ring is directly bonded to the main chain of the polymer), that is, recurring units free of the linker (—CO—O-$A^2$-) include units derived from styrene, 4-chlorostyrene, 4-bromostyrene, 4-methylstyrene, 4-methoxystyrene, 4-acetoxystyrene, 2-hydroxypropylstyrene, 2-vinylnaphthalene, and 3-vinylnaphthalene.

Preferred examples of the recurring units (B4) wherein $t^2$ is 1, that is, having the linker (—CO—O-$A^2$-) are shown below, but not limited thereto. $R^4$ is as defined above.

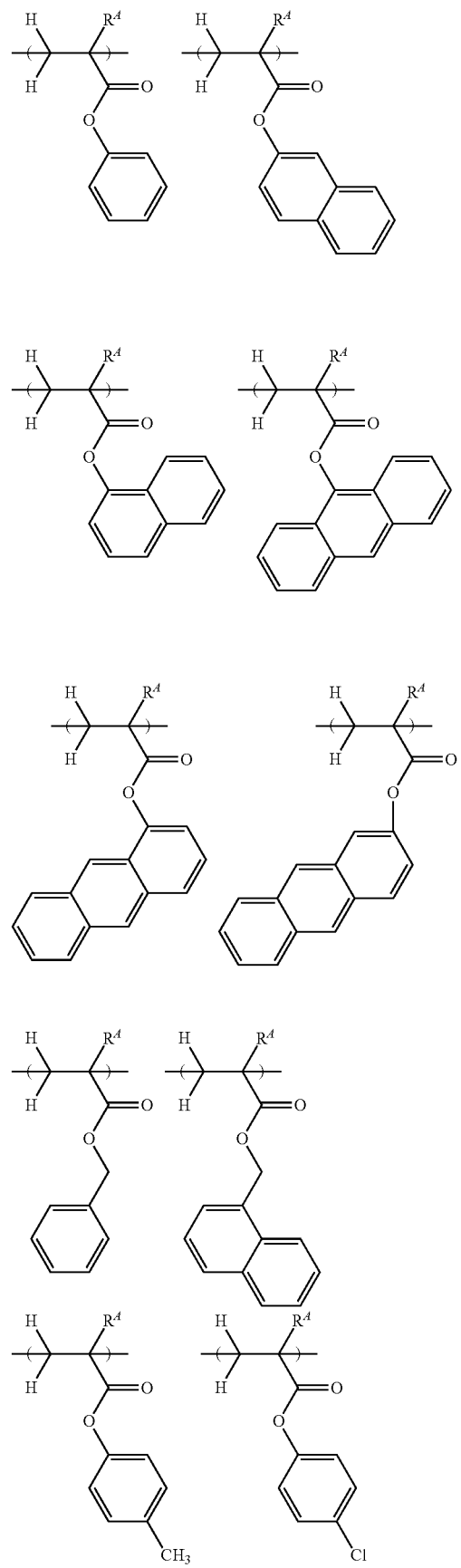

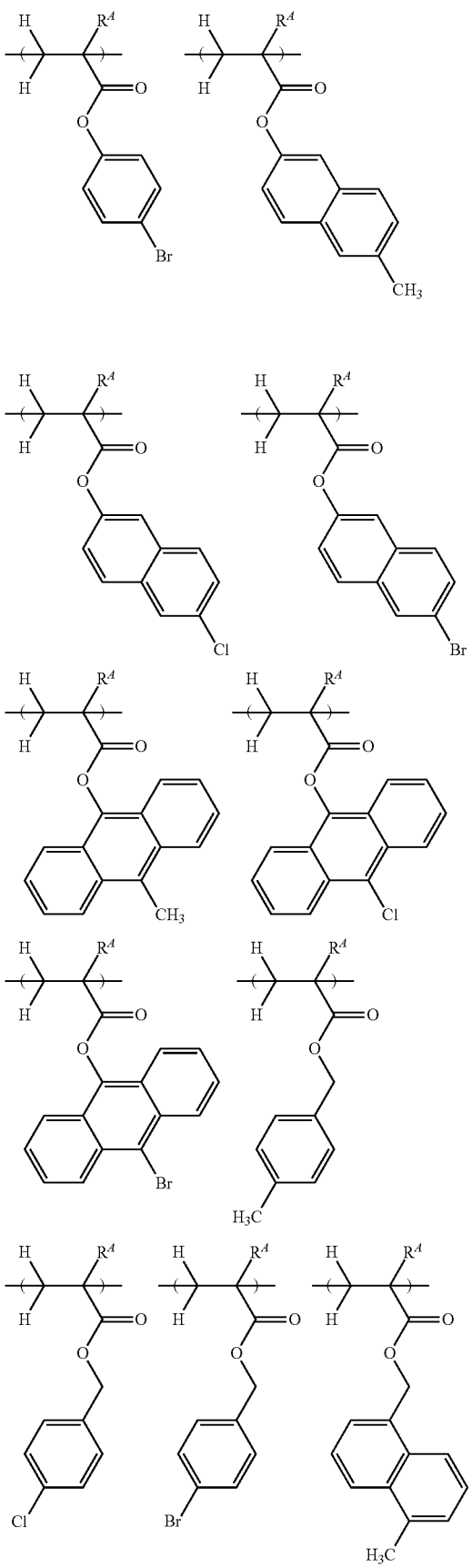

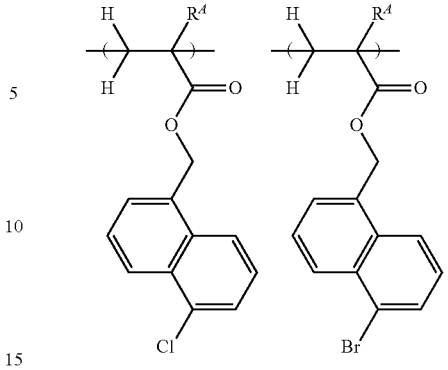

When recurring units of at least one type selected from recurring units (B2) to (B4) are incorporated, better performance is obtained because not only the aromatic ring possesses etching resistance, but the cyclic structure incorporated into the main chain also exerts the effect of improving resistance to EB irradiation during etching and pattern inspection steps.

The recurring units (B2) to (B4) may be of one type or a combination of plural types.

The polymer (B) may further comprise recurring units having the formula (B5). Notably the recurring units having formula (B5) are simply referred to as recurring units (B5), and of the polymers (B), a polymer further comprising recurring units (B5) is referred to as polymer (B').

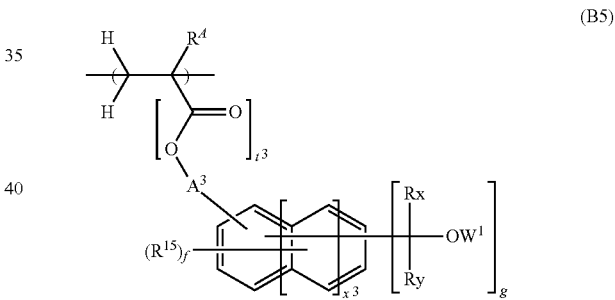

(B5)

Herein $R^A$ is as defined above. $R^{15}$ is each independently halogen, an optionally halogenated $C_2$-$C_8$ acyloxy group, optionally halogenated $C_1$-$C_6$ alkyl group, or optionally halogenated $C_1$-$C_6$ alkoxy group. $A^3$ is a single bond or $C_1$-$C_{10}$ alkanediyl group in which an ether bond may intervene in a carbon-carbon bond. $W^1$ is hydrogen, a $C_1$-$C_{10}$ monovalent aliphatic hydrocarbon group in which an ether bond, carbonyl or carbonyloxy moiety may intervene in a carbon-carbon bond, or an optionally substituted monovalent aromatic group. Rx and Ry are each independently hydrogen, a $C_1$-$C_{15}$ alkyl group which may be substituted with a hydroxy or alkoxy moiety, or an optionally substituted monovalent aromatic group, excluding that Rx and Ry are hydrogen at the same time. Rx and Ry may bond together to form a ring with the carbon atom to which they are attached. The subscript $x^3$ is an integer of 0 to 2, $t^3$ is 0 or 1, f is an integer in the range: $0 \leq f \leq 5+2x^3-g$, and g is an integer of 1 to 3.

Upon exposure to high-energy radiation, the unit (B5) functions such that the acid-eliminatable group undergoes elimination reaction under the action of an acid which is generated by the acid generator. That is, the unit (B5) induces alkali insolubilization and crosslinking reaction between polymer molecules.

Examples of the monovalent aliphatic hydrocarbon and monovalent aromatic groups represented by $W^1$ include methyl, ethyl, propyl, isopropyl, cyclopentyl, cyclohexyl, adamantyl, methylcarbonyl and phenyl.

Preferred structures of Rx and Ry include methyl, ethyl, propyl, butyl and structural isomers thereof, and substituted forms of the foregoing in which some hydrogen is substituted by hydroxy or alkoxy.

The subscript $x^3$ is an integer of 0 to 2. The structure represents a benzene ring when $x^3=0$, a naphthalene ring when $x^3=1$, and an anthracene ring when $x^3=2$.

Preferred examples of the alkanediyl group represented by $A^3$ include methylene, ethylene, propylene, butylene, pentylene, hexylene and structural isomers of a carbon skeleton having branched or cyclic structure. For the alkanediyl group containing an ether bond, in case $t^3=1$ in formula (B5), the ether bond may be incorporated at any position excluding the position between the α- and β-carbons relative to the ester oxygen. In case $t^3=0$, the atom in $A^3$ that bonds with the main chain becomes an ethereal oxygen atom, and a second ether bond may be incorporated at any position excluding the position between the α- and β-carbons relative to that ether bond. Alkanediyl groups having no more than 10 carbon atoms are desirable because of a high solubility in alkaline developer.

Preferred examples of the hydrocarbon portion in the acyloxy, alkyl and alkoxy groups represented by $R^{15}$ include methyl, ethyl, propyl, isopropyl, butyl, pentyl, hexyl and structural isomers of a carbon skeleton having branched or cyclic structure. As long as the carbon count is within the upper limit, good solubility in alkaline developer is available.

Of the recurring units (B5), recurring units having formula (B5-1) or (B5-2) are preferred.

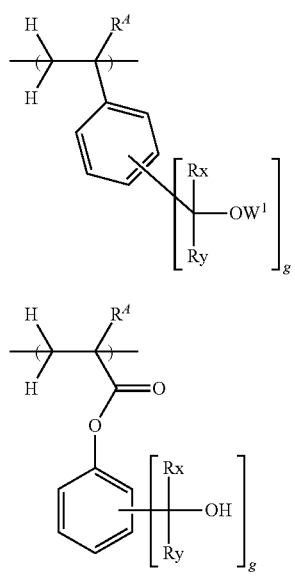

(B5-1)

(B5-2)

Herein $R^A$, Rx, Ry, $W^1$ and g are as defined above.

Preferred examples of the recurring unit (B5) are given below, but not limited thereto. Herein $R^A$ is as defined above.

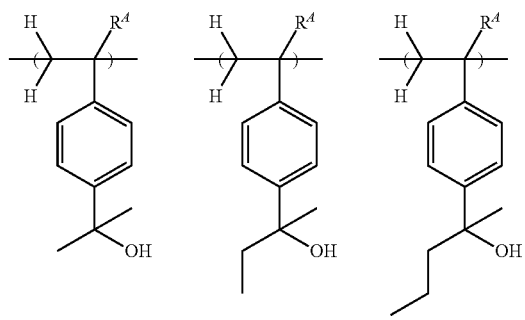

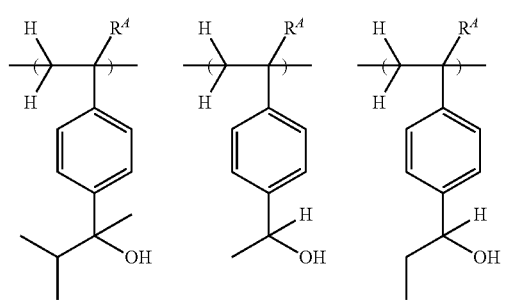

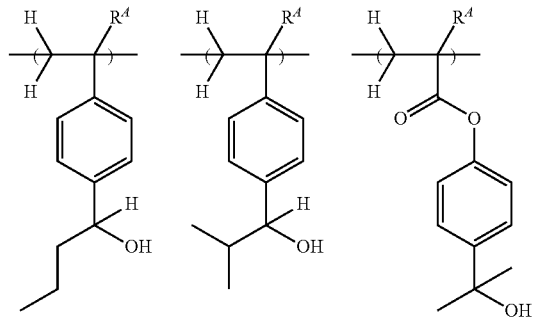

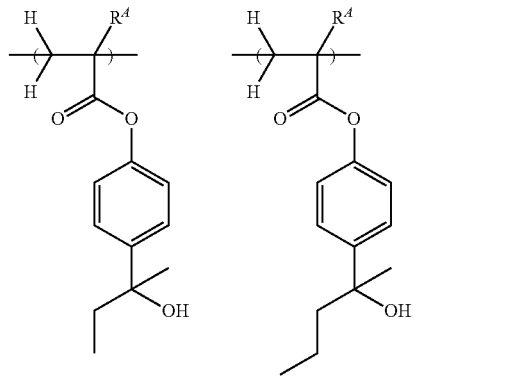

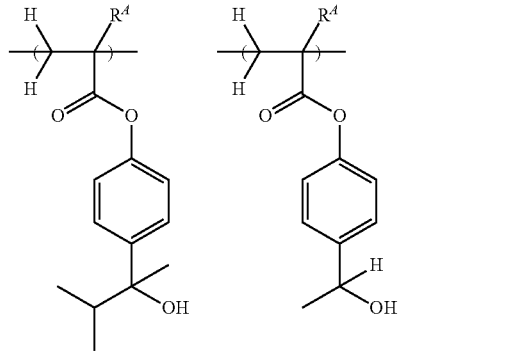

-continued
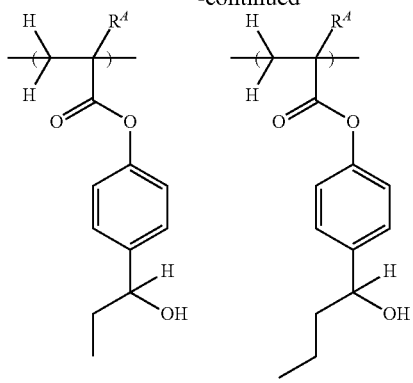
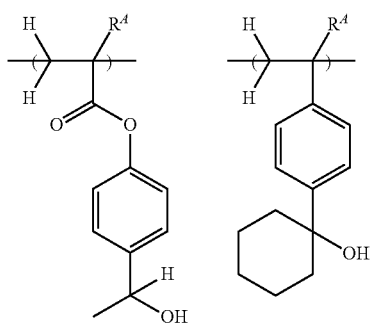
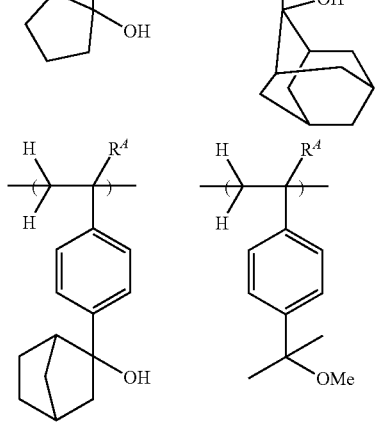
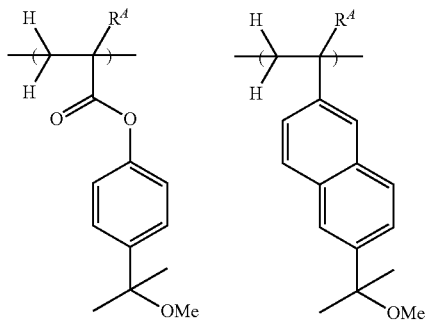
-continued
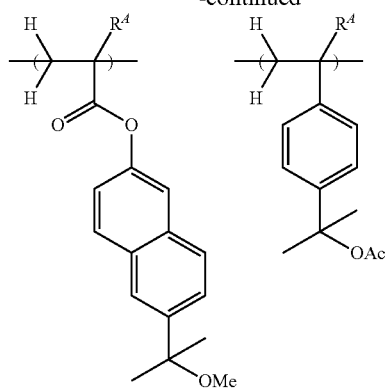
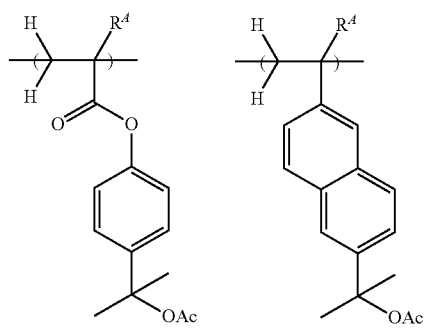
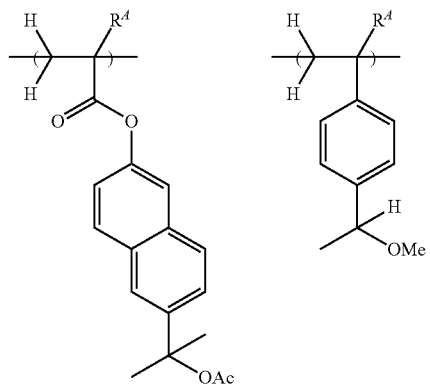
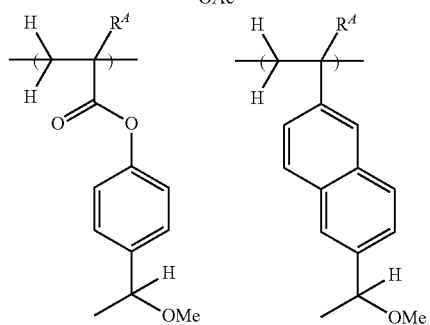

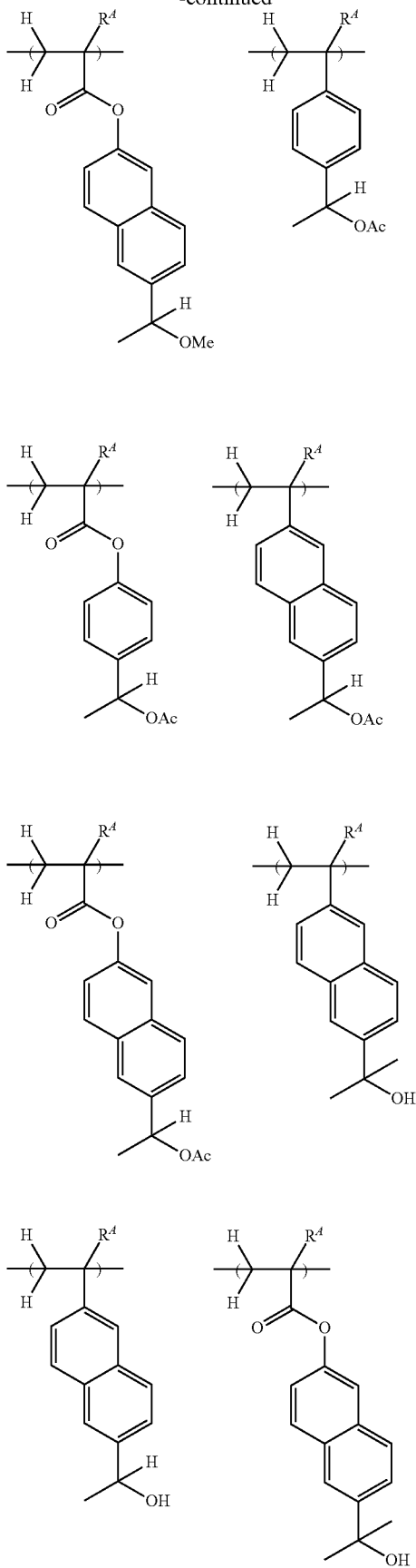
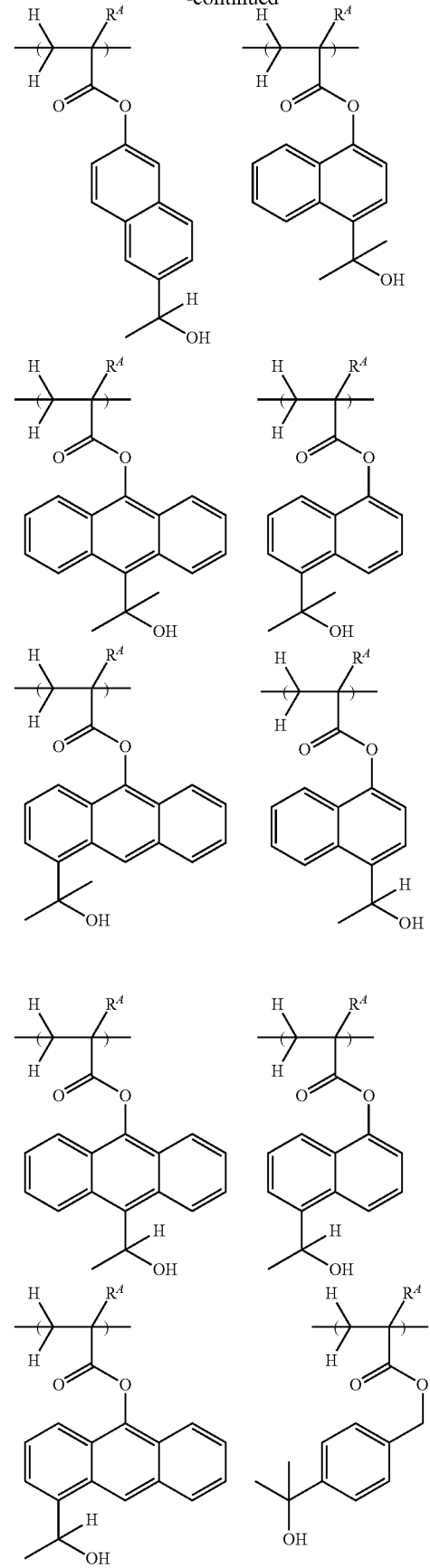

-continued
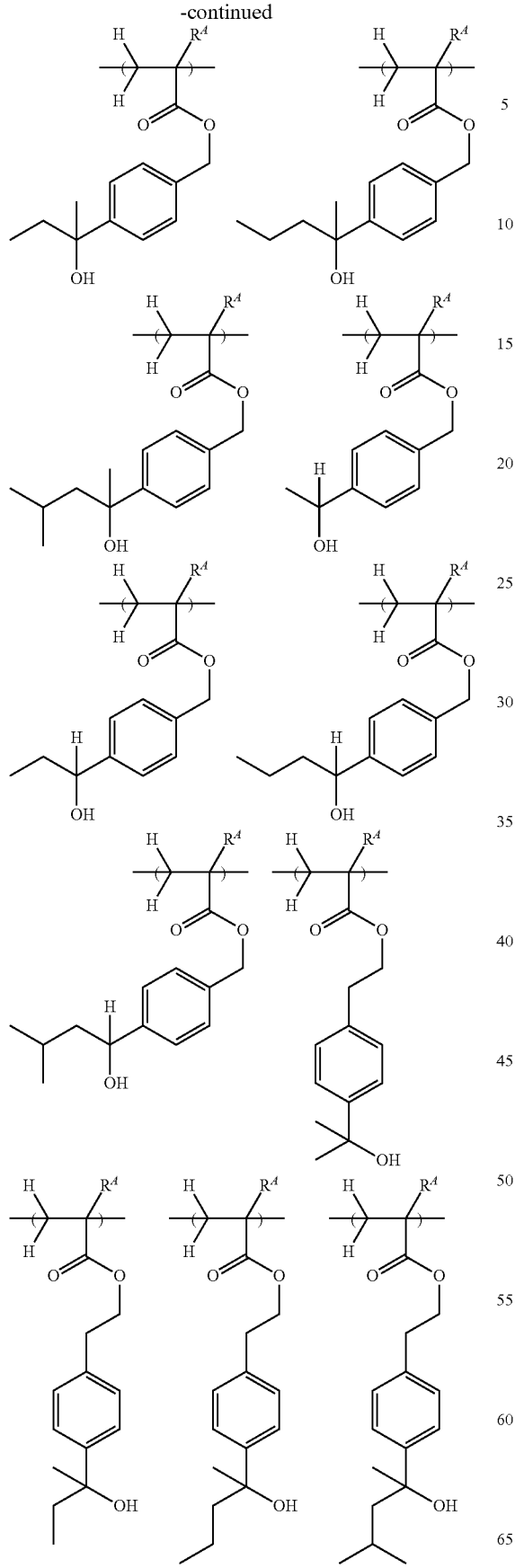
-continued
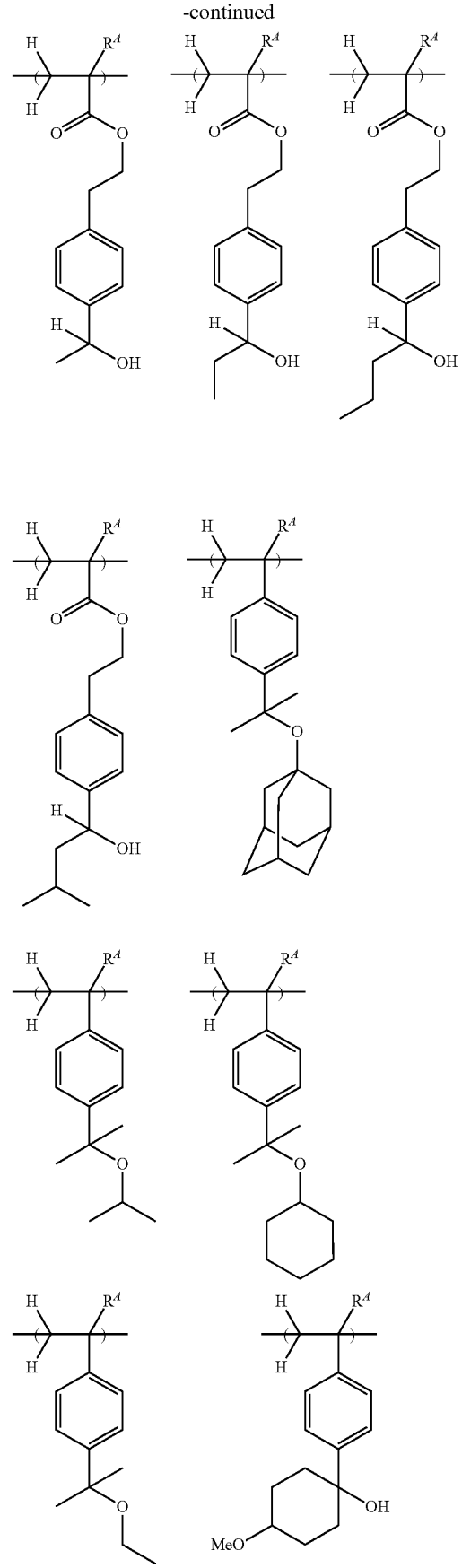

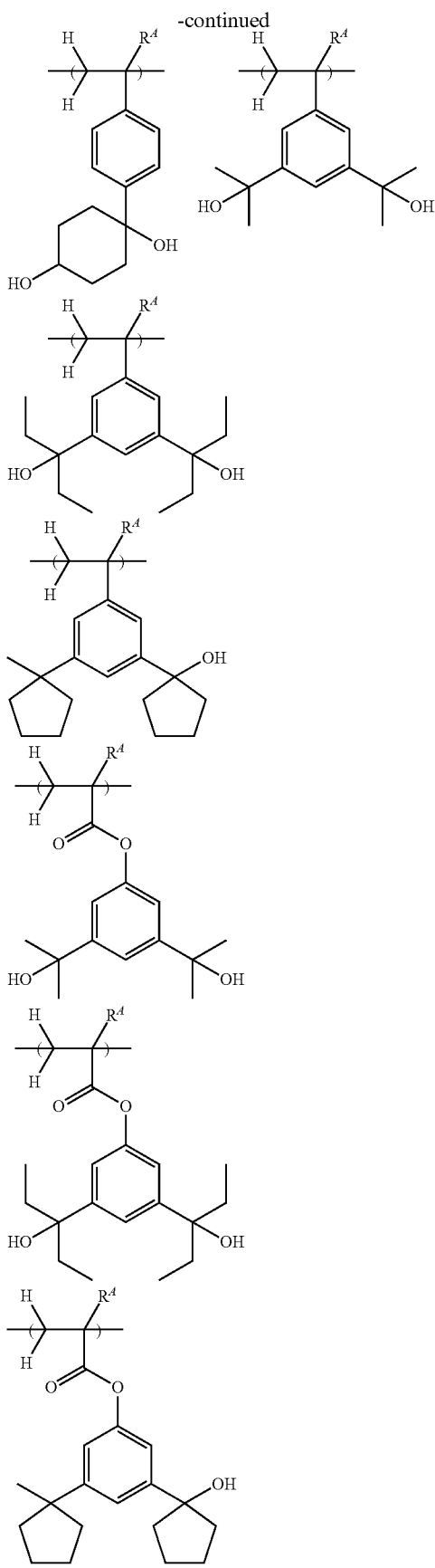

The polymer (B') may further comprise recurring units of at least one type selected from recurring units having formulae (B6) to (B8). Notably these recurring units are simply referred to as recurring units (B6) to (B8).

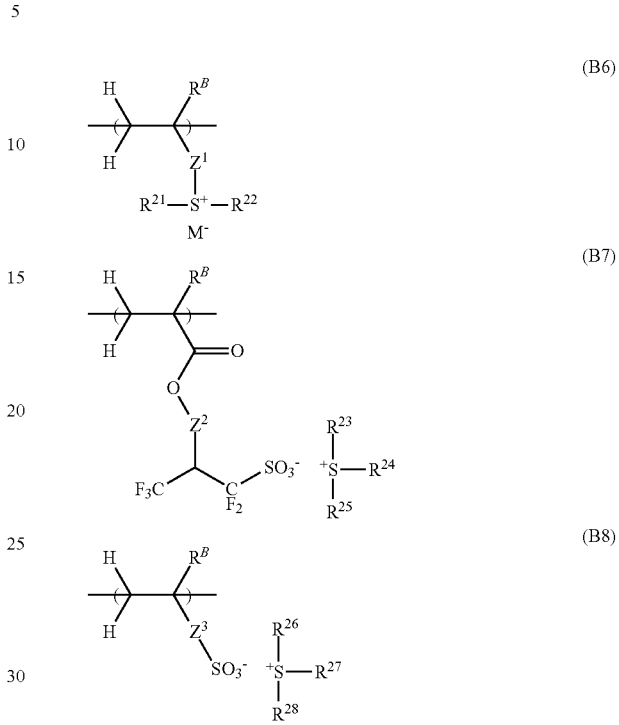

In formulae (B6) to (B8), $R^1$ is each independently hydrogen or methyl. $Z^1$ is a single bond, phenylene group, —O—$Z^{11}$—, —C(=O)—O—$Z^{11}$—, or —C(=O)—NH—$Z^{11}$—, wherein $Z^{11}$ is a $C_1$-$C_6$ alkanediyl, $C_2$-$C_6$ alkenediyl or phenylene group, which may contain a carbonyl moiety, ester bond, ether bond or hydroxy moiety. $Z^2$ is a single bond or —$Z^{21}$—C(=O)—O—, wherein $Z^{21}$ is a $C_1$-$C_{20}$ divalent hydrocarbon group which may contain a heteroatom. $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, wherein $Z^{31}$ is a $C_1$-$C_6$ alkanediyl, $C_2$-$C_6$ alkenediyl or phenylene group, which may contain a carbonyl moiety, ester bond, ether bond or hydroxy moiety.

In formulae (B6) to (B8), $R^{21}$ to $R^{28}$ are each independently a $C_1$-$C_{20}$ monovalent hydrocarbon group which may contain a heteroatom or in which some hydrogen may be substituted by a heteroatom such as oxygen, sulfur, nitrogen or halogen, or in which a heteroatom such as oxygen, sulfur or nitrogen may intervene in a carbon-carbon bond, so that the group may contain a hydroxyl, cyano, carbonyl, ether bond, ester bond, sulfonic acid ester bond, carbonate bond, lactone ring, sultone ring, carboxylic anhydride, or haloalkyl moiety. $R^{21}$ and $R^{22}$ may bond together to form a ring with the sulfur atom to which they are attached, any two or more of $R^{23}$, $R^{24}$ and $R^{25}$ may bond together to form a ring with the sulfur atom to which they are attached, and any two or more of $R^{26}$, $R^{27}$ and $R^{28}$ may bond together to form a ring with the sulfur atom to which they are attached.

In formula (B6), $M^-$ is a non-nucleophilic counter ion.

In formula (B7) wherein $Z^2$ is —$Z^{21}$—C(=O)—O—, $Z^{21}$ is a divalent hydrocarbon group which may contain a heteroatom. Illustrative, non-limiting examples of the hydrocarbon group $Z^{21}$ are given below.

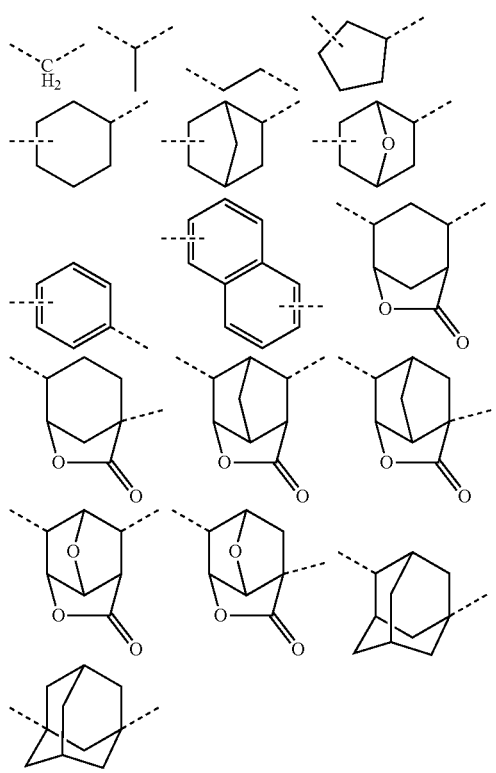

Examples of the sulfonium cation in formulae (B7) and (B8) wherein any two or more of $R^{23}$, $R^{24}$ and $R^{25}$ or any two or more of $R^{26}$, $R^{27}$ and $R^{28}$ bond together to form a ring with the sulfur atom to which they are attached, are shown below, but not limited thereto.

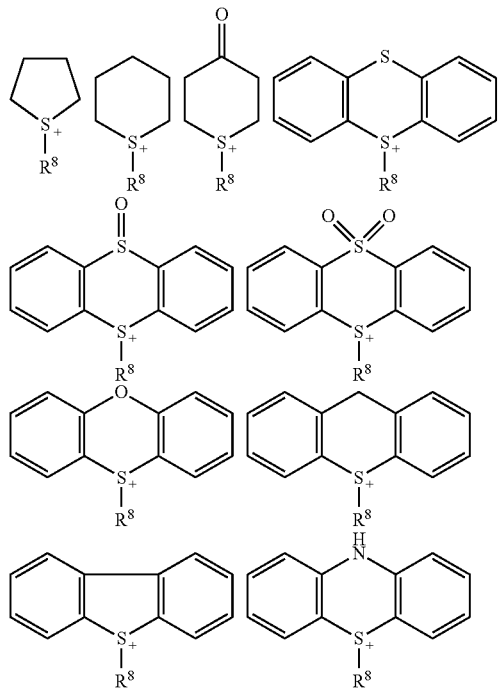

It is noted that $R^{29}$ is the same as defined and exemplified for $R^{21}$ to $R^{28}$.

Specific examples of the sulfonium cation in formulae (B7) and (B8) are shown below, but not limited thereto.

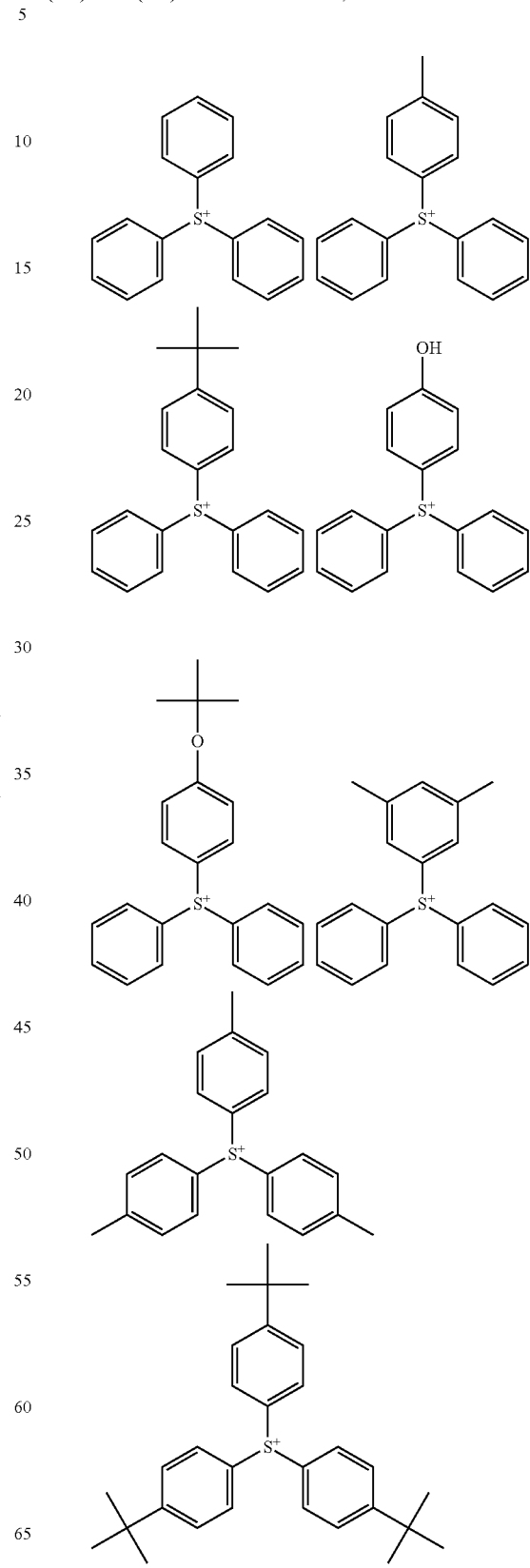

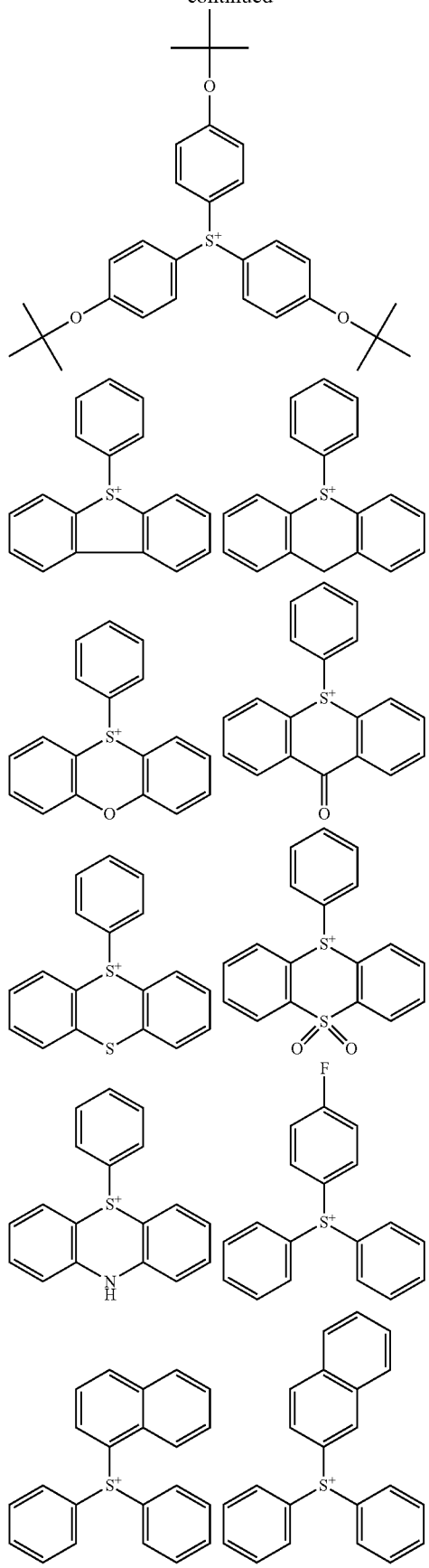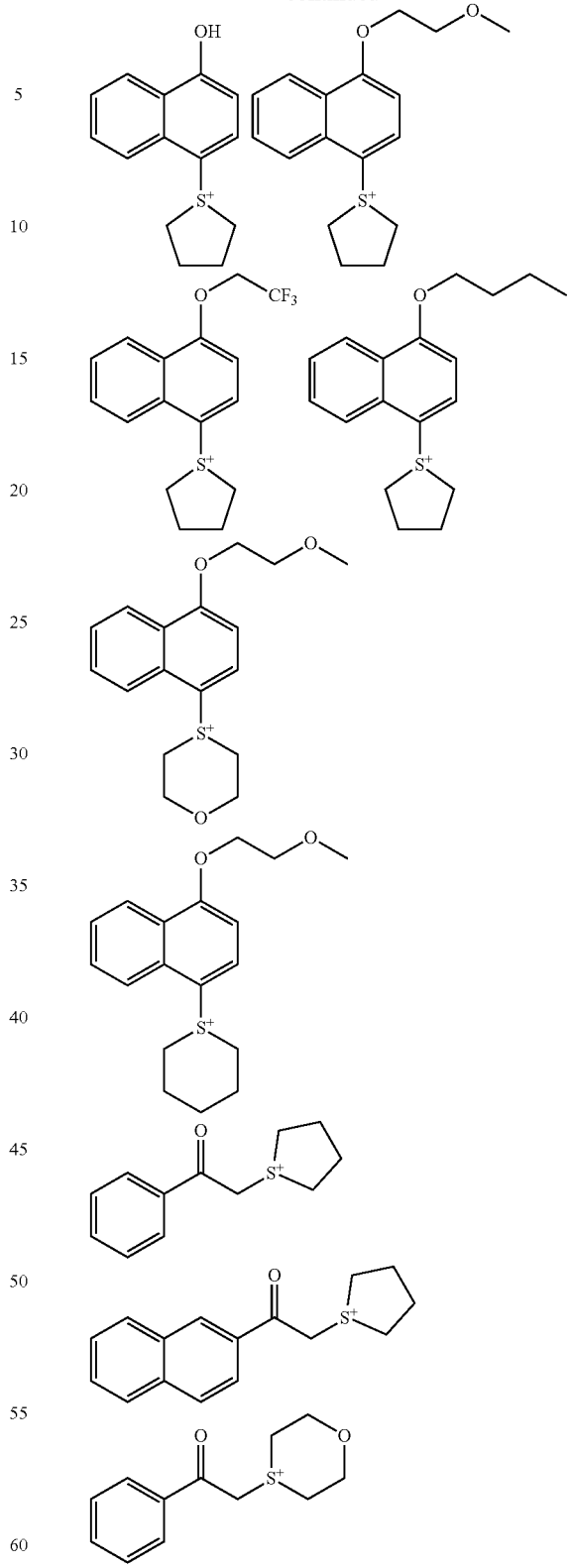
The recurring units (B6) to (B8) are units capable of generating an acid upon receipt of high-energy radiation. With the relevant units bound into a polymer, an appropriate control of acid diffusion becomes possible, and a pattern with minimal LER can be formed. Since the acid-generating unit is bound to a polymer, the phenomenon that acid volatilizes from the exposed region and re-deposits on the unexposed region during bake in vacuum is suppressed. This is effective for reducing LER and for suppressing unwanted negative tone reaction in the unexposed region for thereby reducing defects. The content of recurring units (B6) to (B8) is preferably 0.5 to 20 mol % based on the overall recurring units of polymer (B').

In the polymer, (meth)acrylate and other recurring units having an adhesive group such as lactone structure may be incorporated for fine adjustment of properties of a resist film, though they are optional.

In polymer (B), an appropriate content of recurring units (B1) is 50 to 95 mol %, more preferably 70 to 85 mol %; an appropriate content of recurring units (B2) to (B4) is 5 to 50 mol %, more preferably 15 to 30 mol %; an appropriate content of other recurring units is 0 to 20 mol %, more preferably 0 to 10 mol %.

Where the polymer (B') is free of recurring units (B6) to (B8), the polymer preferably contains 25 to 95 mol %, more preferably 40 to 85 mol % of recurring units (B1). An appropriate content of recurring units (B2) to (B4) is 0 to 30 mol %, more preferably 5 to 20 mol %. An appropriate content of recurring units (B5) is 5 to 45 mol %, more preferably 10 to 40 mol %. The other recurring units may be incorporated in a range of 0 to 20 mol %, preferably 0 to 10 mol %.

Where the polymer (B') contains recurring units (B6) to (B8), the polymer preferably contains 25 to 94.5 mol %, more preferably 50 to 85 mol % of recurring units (B1). An appropriate content of recurring units (B2) to (B4) is 0 to 20 mol %, more preferably 3 to 15 mol %. An appropriate content of recurring units (B5) is 5 to 35 mol %, more preferably 10 to 25 mol %. An appropriate content of recurring units (B6) to (B8) is 0.5 to 20 mol %, more preferably 2 to 10 mol %. The other recurring units may be incorporated in a range of 0 to 20 mol %, preferably 0 to 10 mol %.

Also preferably recurring units (B1) to (B5) account for at least 60 mol %, more preferably at least 70 mol % of the overall recurring units of the polymer. This range ensures that the polymer has necessary properties as the inventive negative resist composition.

As the polymer (B') containing recurring units (B6) to (B8), a polymer comprising recurring units having the formula (B1-1), recurring units having the formula (B5-1), and recurring units having the formula (B7) is preferred.

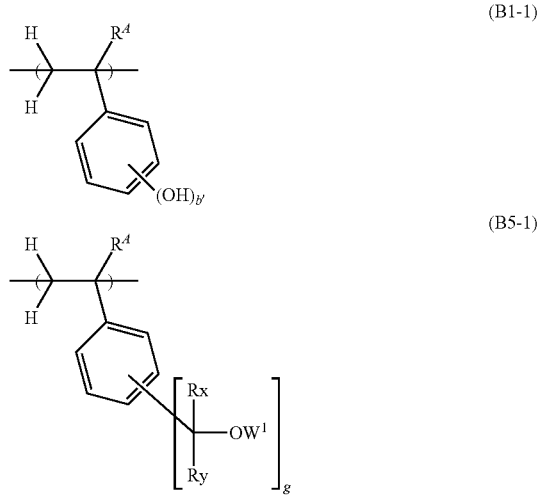

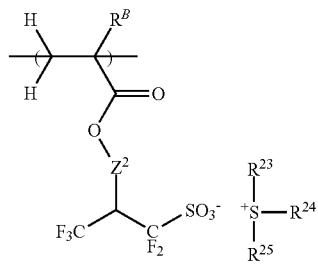

Herein $R^A$, R, $Z^2$, $R^{23}$, $R^{24}$, $R^{25}$, Rx, Ry, $W^1$, b', and g are as defined above.

Where the polymer (B') is used as the base polymer (B), it may be a mixture of a polymer free of recurring units (B6) to (B8) and a polymer comprising recurring units (B6) to (B8). In this embodiment, the polymer free of recurring units (B6) to (B8) is preferably used in an amount of 2 to 5,000 parts, more preferably 10 to 1,000 parts by weight per 100 parts by weight of the polymer comprising recurring units (B6) to (B8).

The polymer may be synthesized by combining suitable monomers optionally protected with a protective group, copolymerizing them in the standard way, and effecting deprotection reaction if necessary. The copolymerization reaction is preferably radical polymerization or anionic polymerization though not limited thereto. For the polymerization reaction, reference may be made to WO 2006/121096, JP-A 2004-115630, JP-A 2008-102383, and JP-A 2008-304590.

The polymer should preferably have a Mw of 2,000 to 50,000, and more preferably 3,000 to 20,000. A Mw of at least 2,000 eliminates the risk that pattern features are rounded at their top, inviting degradations of resolution and LER. A Mw of up to 50,000 eliminates the risk that LER is increased. A Mw of up to 20,000 is preferable particularly when a pattern with a line width of up to 100 nm is formed. As used herein, Mw is measured by GPC versus polystyrene standards.

The polymer preferably has a narrow molecular weight distribution or dispersity (Mw/Mn) of 1.0 to 2.0, more preferably 1.0 to 1.8. A polymer with such a narrow dispersity eliminates any foreign particles left on the pattern or profile degradation of the pattern after development.

(C) Crosslinker

When only polymer (B) is used as the base polymer in the negative resist composition, a crosslinker is preferably added. When the base polymer contains polymer (B'), a crosslinker need not be added.

Suitable crosslinkers which can be used herein include melamine compounds, guanamine compounds, glycoluril compounds and urea compounds having substituted thereon at least one group selected from among methylol, alkoxymethyl and acyloxymethyl groups, epoxy compounds, isocyanate compounds, azide compounds, and compounds having a double bond such as an alkenyl ether group. These compounds may be used as an additive or introduced into a polymer side chain as a pendant. Hydroxy-containing compounds may also be used as the crosslinker.

Of the foregoing crosslinkers, examples of suitable epoxy compounds include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

An appropriate amount of the crosslinker used is 2 to 50 parts, and more preferably 5 to 30 parts by weight per 100 parts by weight of the base polymer. As long as the amount of the crosslinker is in the range, the risk of resolution being reduced by forming bridges between pattern features is mitigated. The crosslinkers may be used alone or in admixture.

(D) Organic Solvent

The negative resist composition may further comprise (D) an organic solvent. The organic solvent used herein is not particularly limited as long as the components are soluble therein. Examples of the organic solvent are described in JP-A 2008-111103, paragraphs [0144] to [0145] (U.S. Pat. No. 7,537,880). Specifically, exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, propylene glycol monomethyl ether, cyclohexanone, ethyl lactate, γ-butyrolactone, and mixtures thereof.

An appropriate amount of the organic solvent (D) used is 200 to 10,000 parts, more preferably 400 to 5,000 parts by weight per 100 parts by weight of the base polymer (B).

(E) Acid Generator

The negative resist composition may further comprise (E) an acid generator in order that the composition function as a chemically amplified negative resist composition. The acid generator is typically a compound capable of generating acid in response to actinic light or radiation (known as photoacid generator). It may be any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators. These PAGs may be used alone or in admixture of two or more.

Suitable PAGs include those described in JP-A 2008-111103, paragraphs [0122]-[0142]. Among others, arenesulfonate type PAGs are preferred because they generate acids having an appropriate strength to promote reaction of base polymer (B) with crosslinker (C). The PAG capable of generating an acid having a pKa value in the range of −3.0 to 1.5, more preferably −1.0 to 1.5 is preferred because the effect of improving LER by combining the generated acid with the onium salt (A) to induce exchange reaction is achievable.

The preferred PAGs are sulfonium salts having a sulfonate anion of the structure shown below. Notably the cation that pairs with the anion is as exemplified for the sulfonium cation in formulae (B7) and (B8).

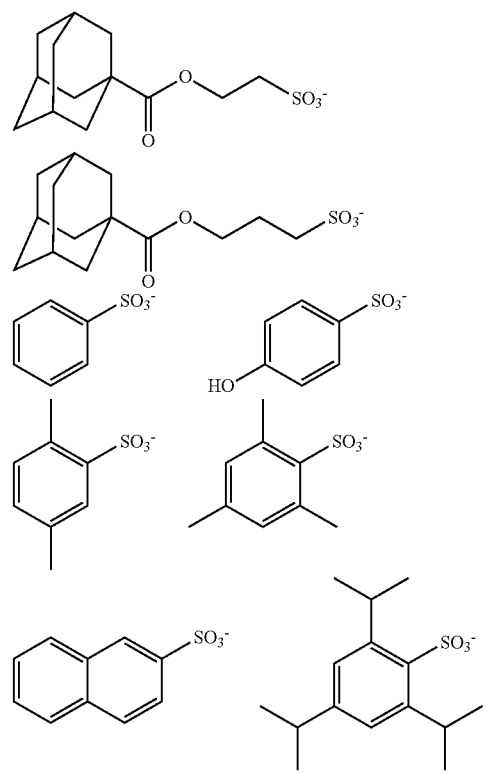

-continued
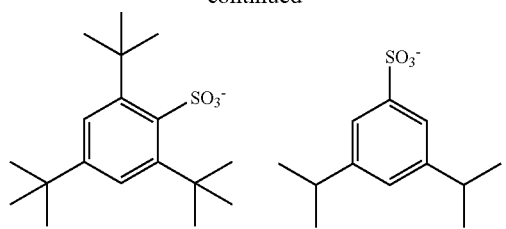
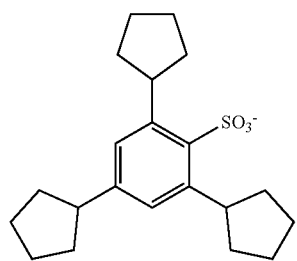
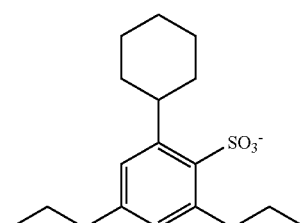
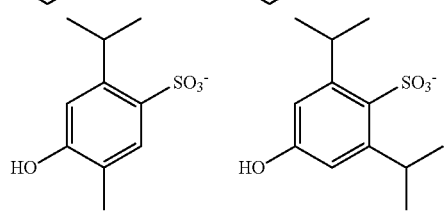
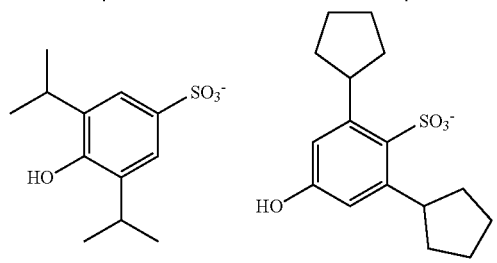
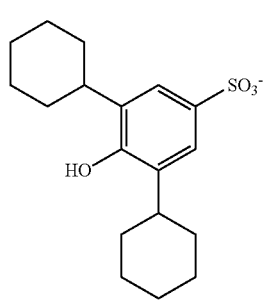
-continued
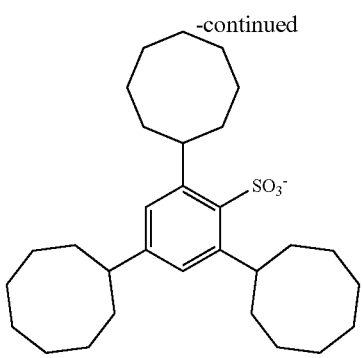
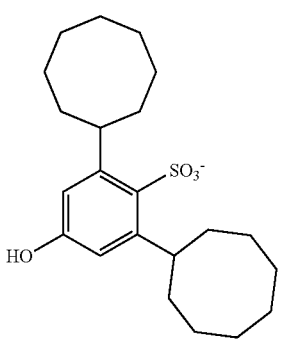
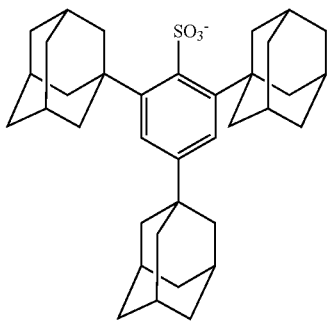
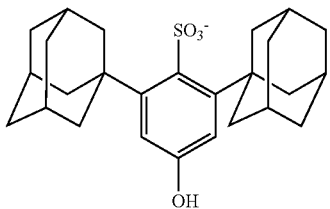
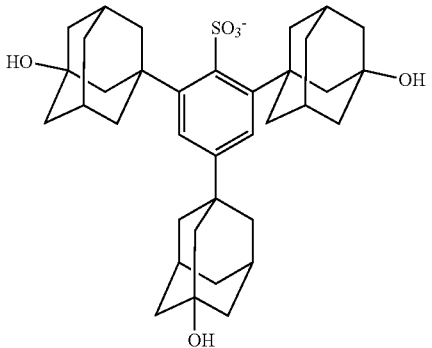

47
-continued
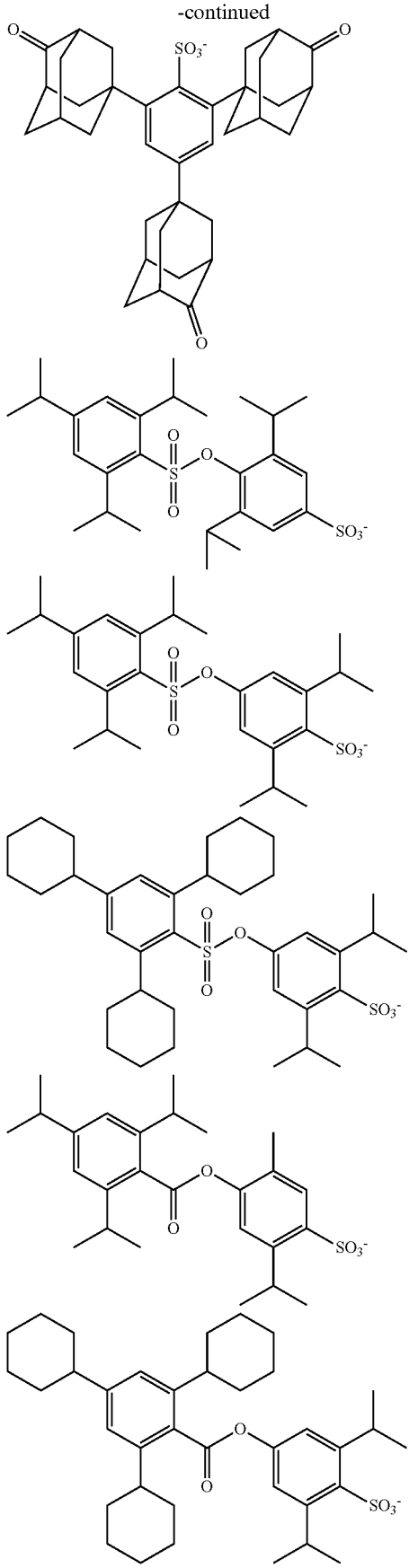
48
-continued
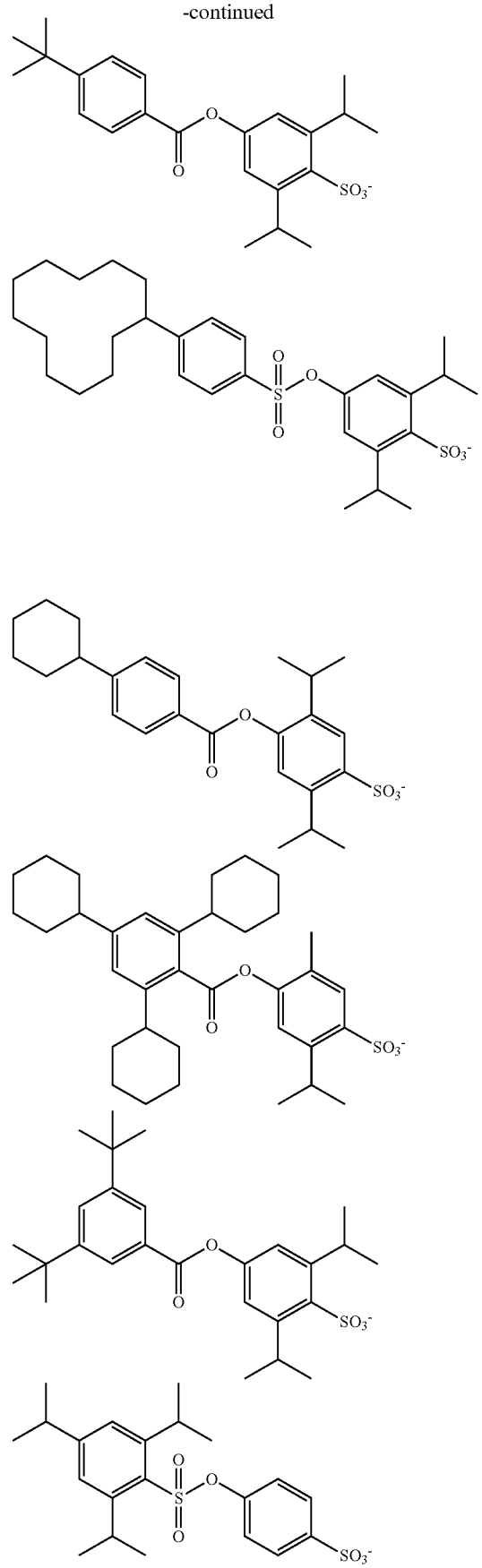

-continued
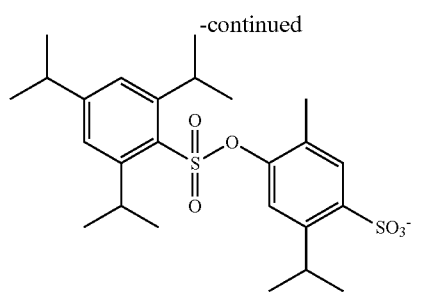
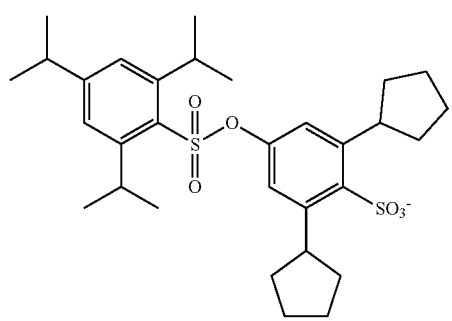
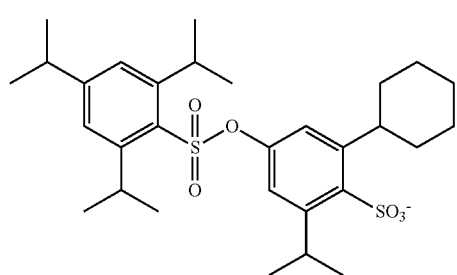
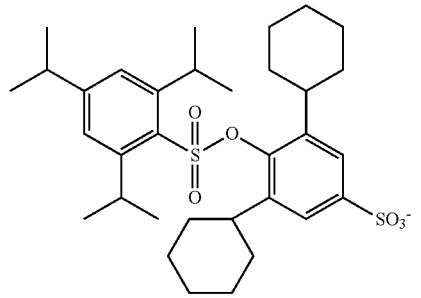
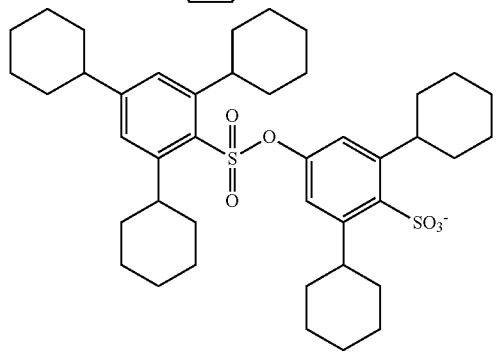
-continued
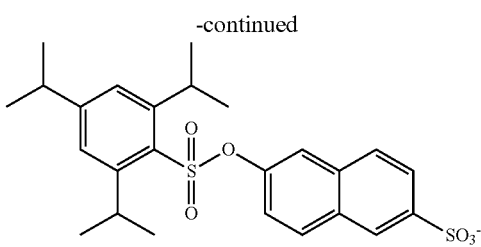
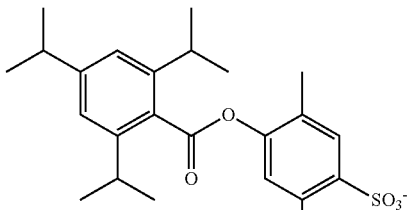
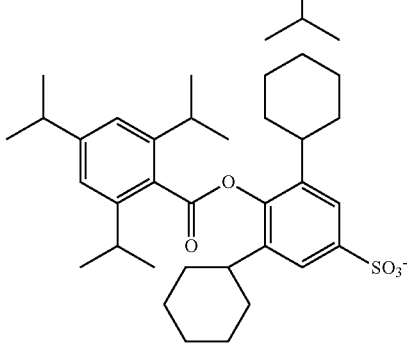
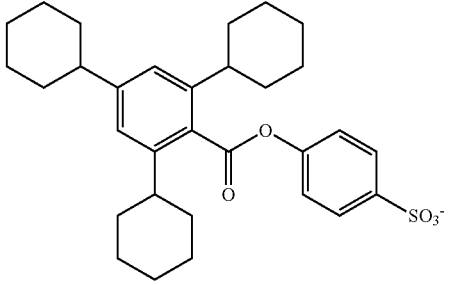
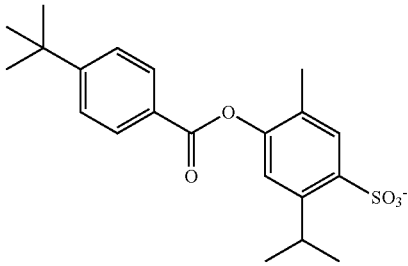
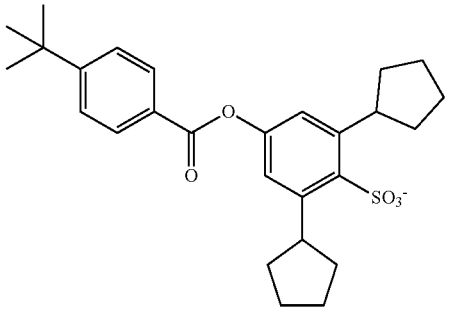

51
-continued
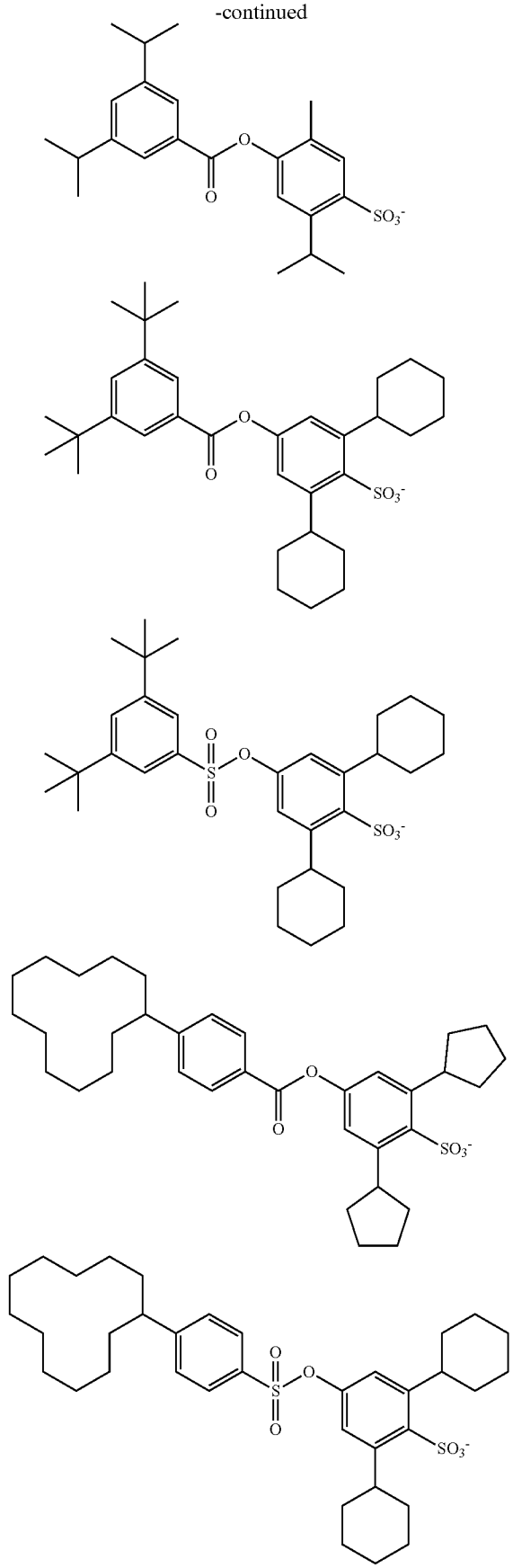
52
-continued
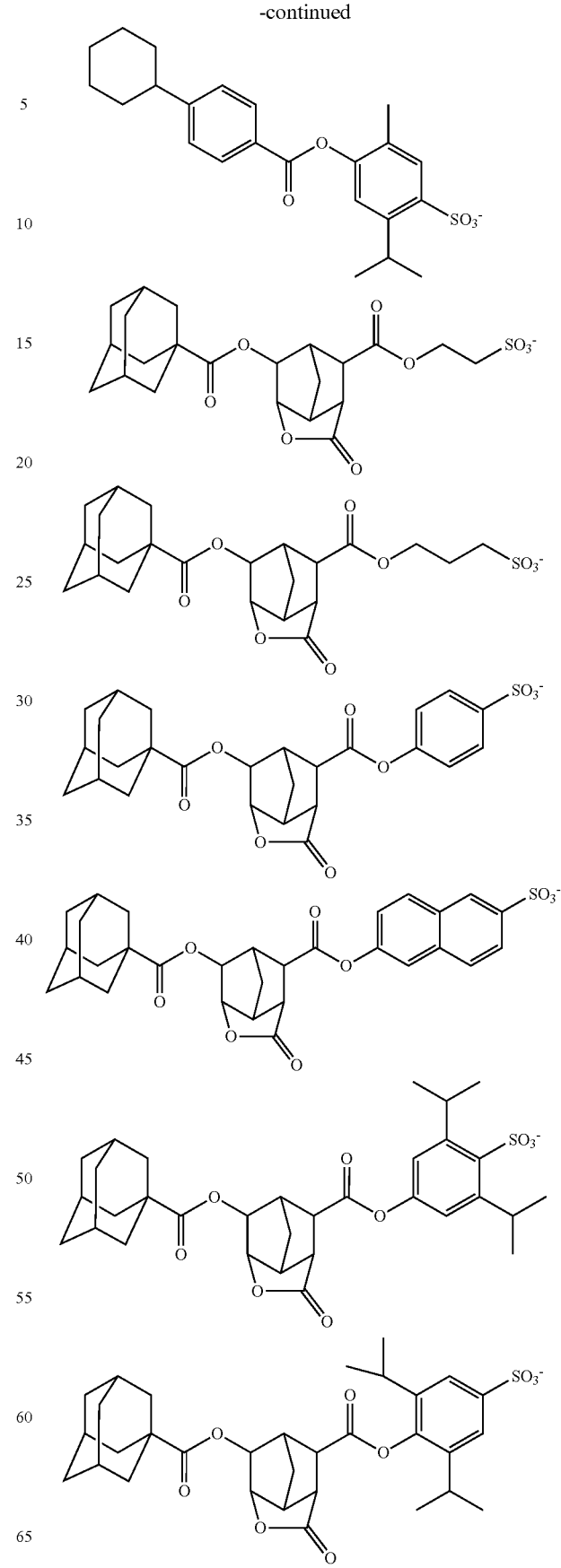

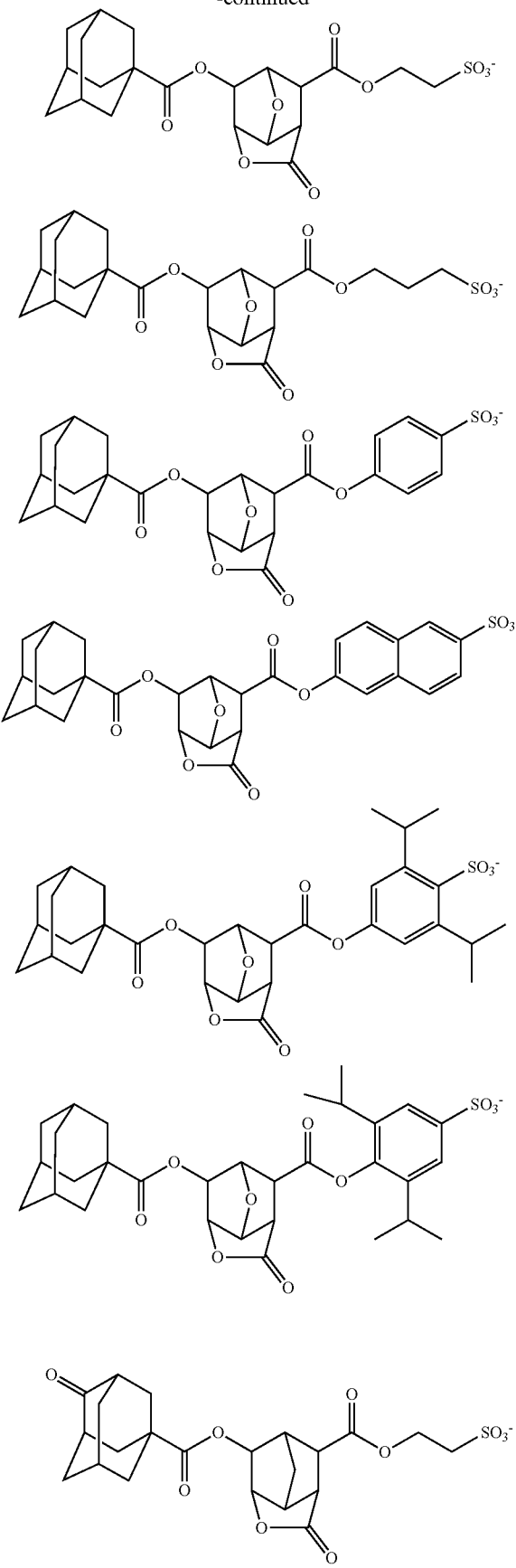
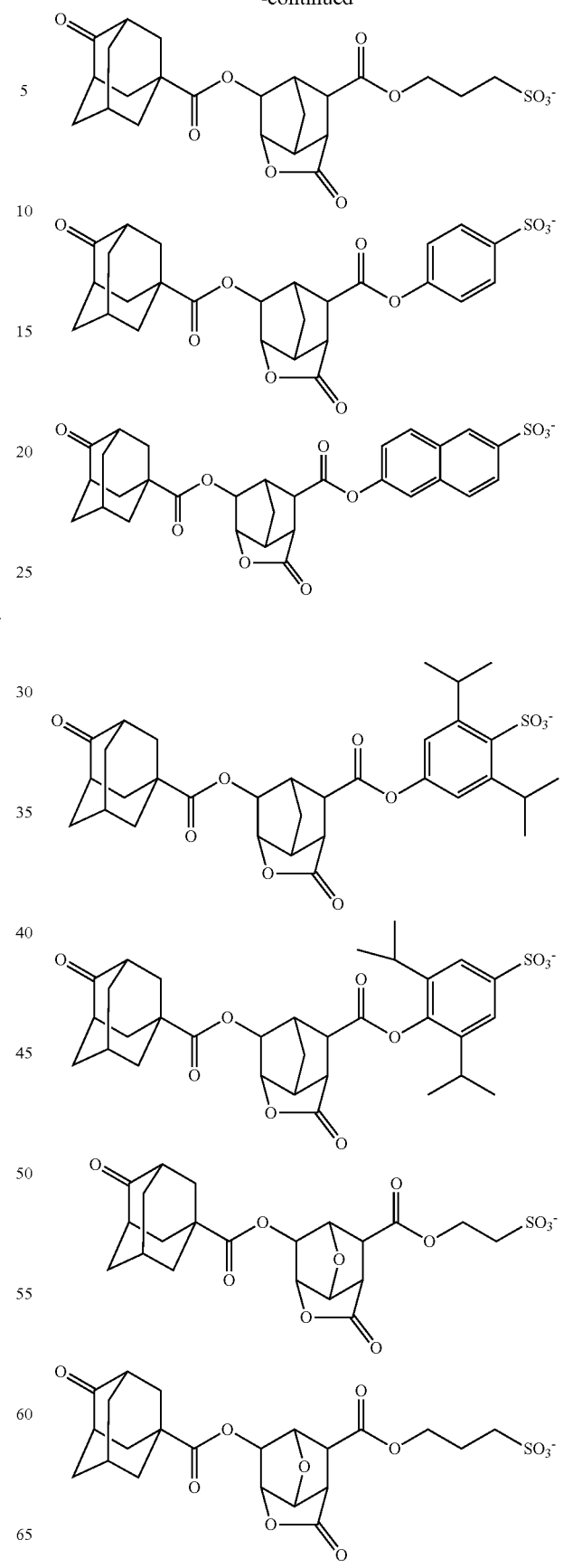

-continued

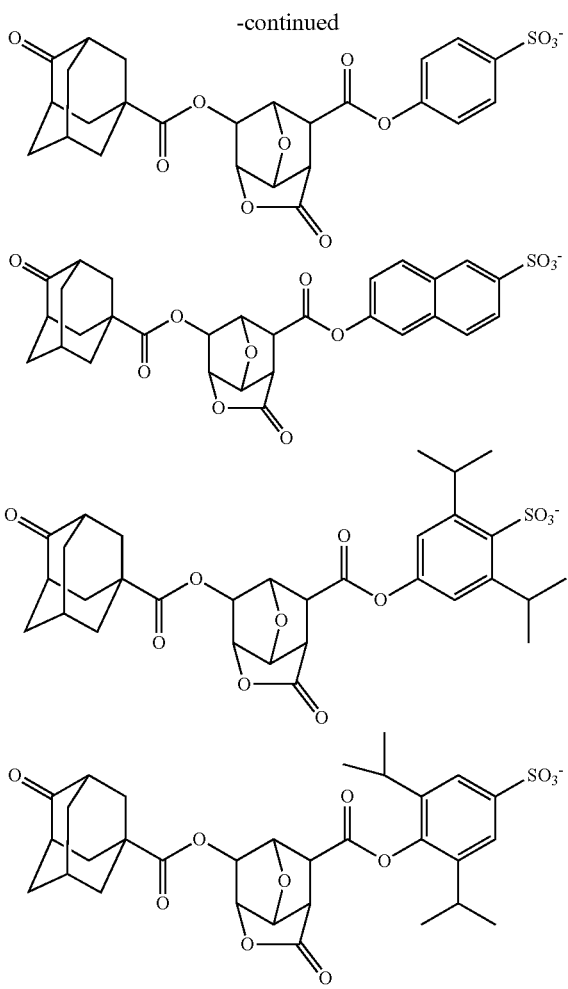

An appropriate amount of the acid generator (E) used is 2 to 20 parts, more preferably 5 to 15 parts by weight per 100 parts by weight of the base polymer (B). Where the base polymer contains recurring units (B6) to (B8), the PAG may be omitted.

(F) Basic Compound

In the resist composition, (F) a basic compound may be added as the quencher (other than component (A)) for the purpose of correcting a pattern profile or the like. The basic compound is effective for controlling acid diffusion. Even when the resist film is applied to a processable substrate having an outermost surface layer made of a chromium-containing material, the basic compound is effective for minimizing the influence of the acid generated in the resist film on the chromium-containing material.

Numerous basic compounds are known useful including primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, carbamate derivatives, and ammonium salts. Examples are described in JP 4575479, for example, and any such compounds are useful. Of the foregoing basic compounds, preferred are tris[2-(methoxymethoxy)ethyl]amine, tris[2-(methoxymethoxy)ethyl]amine-N-oxide, morpholine derivatives and imidazole derivatives.

An appropriate amount of the basic compound (F) added is 0 to 10 parts, and more preferably 0 to 5 parts by weight per 100 parts by weight of the base polymer (B). The basic compounds may be used alone or in admixture.

(G) Surfactant

In the resist composition, any of surfactants commonly used for improving coating characteristics to the processable substrate may be added as an optional component. Numerous surfactants are known in the art including those described in JP-A 2004-115630, for example. A choice may be made with reference to such patent documents. An appropriate amount of the surfactant (G) used is 0 to 2 parts by weight per 100 parts by weight of the base polymer (B).

Process

A further embodiment of the invention is a resist pattern forming process comprising the steps of applying the resist composition defined above onto a substrate to form a resist film thereon, exposing the resist film patternwise to high-energy radiation, and developing the resist film in an alkaline developer to form a resist pattern.

Pattern formation using the negative resist composition of the invention may be performed by well-known lithography processes. In general, the resist composition is first applied onto a processable substrate such as a substrate for IC fabrication (e.g., Si, SiO, $SiO_2$, SiN, SiON, TiN, WSi, BPSG, SOG, organic antireflective coating, etc.) or a substrate for mask circuit fabrication (e.g., Cr, CrO, CrON, $MoSi_2$, Si, SiO, $SiO_2$, etc.) by a suitable coating technique such as spin coating. The coating is prebaked on a hotplate at a temperature of 60 to 150° C. for 1 to 20 minutes, preferably at 80 to 140° C. for 1 to 10 minutes to form a resist film of 0.03 to 2 µm thick.

An anti-charging film comprising a conductive polymer may be formed on the resist film. The anti-charging film is effective for preventing a charging phenomenon or charge buildup in the resist film during EB writing for thereby achieving a significant improvement in writing position accuracy. The anti-charging film is typically formed of a conductive polymer such as polyaniline or polythiophene as described in JP-A 2016-200634.

Then the resist film is exposed patternwise to high-energy radiation such as UV, deep-UV, excimer laser (KrF, ArF), EUV, x-ray, γ-ray or synchrotron radiation or EB. On use of UV, deep-UV, EUV, excimer laser, x-ray, γ-ray or synchrotron radiation as the high-energy radiation, the resist film is exposed through a mask having a desired pattern, preferably in a dose of 1 to 200 $mJ/cm^2$, more preferably 10 to 100 $mJ/cm^2$. On use of EB, a pattern may be written directly or through a mask having the desired pattern, preferably in a dose of 1 to 300 $\mu C/cm^2$, more preferably 10 to 200 $\mu C/cm^2$. The resist composition of the invention is especially effective in the EUV or EB lithography.

The exposure may be performed by conventional lithography whereas the immersion lithography of holding a liquid between the mask and the resist film may be employed if desired. In the case of immersion lithography, a protective film which is insoluble in water may be used.

The resist film is then baked (PEB) on a hotplate at 60 to 150° C. for 1 to 20 minutes, preferably at 80 to 140° C. for 1 to 10 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

From the resist composition, a pattern with a high resolution and minimal LER may be formed. The resist composition is effectively applicable to a substrate, specifically a substrate having a surface layer of material to which a resist film is less adherent and which is likely to invite pattern stripping or pattern collapse, and particularly a substrate having sputter deposited thereon metallic chromium or a chromium compound containing at least one light element selected from oxygen, nitrogen and carbon or a substrate having an outermost surface layer of $SiO_x$. The invention is especially effective for pattern formation on a photomask blank as the substrate.

EXAMPLES

Examples of the invention are given below by way of illustration and not by way of limitation. The abbreviation "pbw" is parts by weight. THF stands for tetrahydrofuran, and DMAP for dimethylaminopyridine. The copolymer composition is expressed by a molar ratio. Mw is measured versus polystyrene standards by GPC using THF solvent.

[1] Synthesis of Onium Salt

Example 1-1

Synthesis of Salt-1

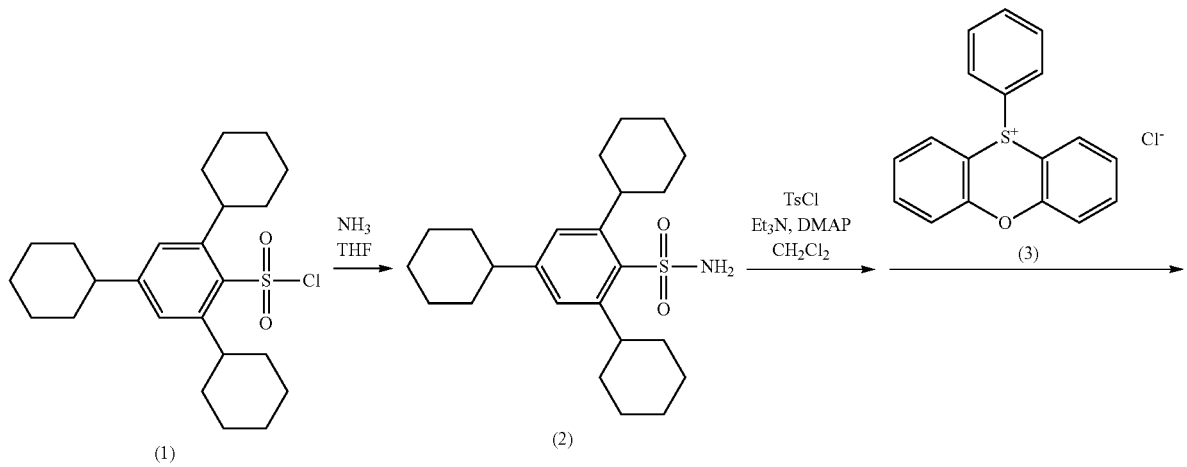

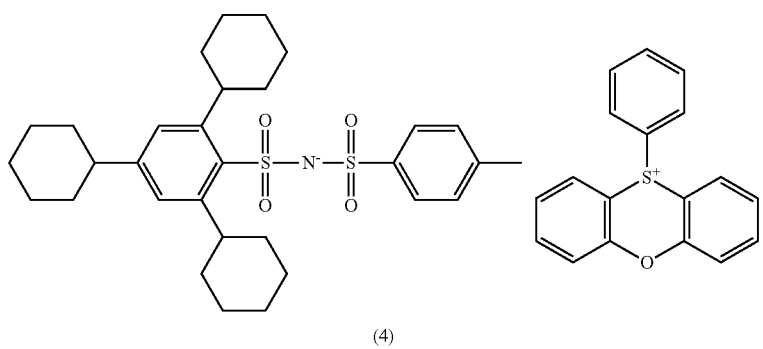

In 1,000 g of THF was dissolved 100 g of 2,4,6-tricyclohexylbenzenesulfonyl chloride (1). The solution was combined with 28.7 g of 28 wt % NH₃ aqueous solution and stirred at room temperature for 12 hours. Then 3,000 g of methylene chloride was added to the solution. The organic layer was taken out, washed with water, and concentrated under reduced pressure, obtaining 90.1 g of the desired compound, 2,4,6-tricyclohexylbenzenesulfonamide (2) as white solid (yield 95%).

In 200 g of methylene chloride (CH$_2$Cl$_2$) was dissolved 20 g of 2,4,6-tricyclohexylbenzenesulfonamide (2). Then 11.3 g of p-toluenesulfonyl chloride (TsCl) and 1.2 g of DMAP were added. Under ice cooling, 7.5 g of triethylamine (Et$_3$N) was added dropwise to the solution, which was stirred at room temperature for 6 hours. Thereafter, 180 g of 5 wt % HCl aqueous solution and 200 g of methylene chloride were added to the solution. The organic layer was taken out, washed with water, and combined with 517 g of 6 wt % 10-phenylphenoxathiinium chloride aqueous solution. The organic layer was taken out again, washed with water, and concentrated under reduced pressure. Toluene was added to the concentrate, followed by concentration again. The solid precipitate was washed with diisopropyl ether. The solid was dried in vacuum, obtaining 27.3 g of the target compound, 10-phenylphenoxathiinium 2,4,6-tricyclohexyl-N-(p-toluenesulfonyl)-benzenesulfonamidate (4) as white solid (yield 66%). This is designated Salt-1.

Example 1-2

Synthesis of Salt-2

The same procedure as in Example 1-1 was repeated except that 2,4,6-triisopropylbenzenesulfonyl chloride was used instead of 2,4,6-tricyclohexylbenzenesulfonyl chloride, and benzenesulfonyl chloride was used instead of p-toluenesulfonyl chloride. There was synthesized 10-phenylphenoxathiinium 2,4,6-triisopropyl-N-(benzenesulfonyl)benzenesulfonamidate, designated Salt-2.

Example 1-3

Synthesis of Salt-3

The same procedure as in Example 1-1 was repeated except that 2,5-dimethylbenzenesulfonyl chloride was used instead of 2,4,6-tricyclohexylbenzenesulfonyl chloride, methanesulfonyl chloride was used instead of p-toluenesulfonyl chloride, and a triphenylsulfonium chloride aqueous solution was used instead of the 10-phenylphenoxathiinium chloride aqueous solution. There was synthesized triphenylsulfonium 2,5-dimethyl-N-(methanesulfonyl)benzenesulfonamidate, designated Salt-3.

Example 1-4

Synthesis of Salt-4

The same procedure as in Example 1-1 was repeated except that 2,4,6-triisopropylbenzenesulfonyl chloride was used instead of 2,4,6-tricyclohexylbenzenesulfonyl chloride, trifluoromethanesulfonyl chloride was used instead of p-toluenesulfonyl chloride, and a triphenylsulfonium chloride aqueous solution was used instead of the 10-phenylphenoxathiinium chloride aqueous solution. There was synthesized triphenylsulfonium 2,4,6-triisopropyl-N-(trifluoromethanesulfonyl)-benzenesulfonamidate, designated Salt-4.

Example 1-5

Synthesis of Salt-5

Methanesulfonamide, 14.3 g, was dissolved in 100 g of water, 25.1 g of 10-camphorsulfonyl chloride was added thereto, and 8.4 g of potassium hydroxide was added thereto. The mixture was stirred at room temperature for 3 hours, whereupon 1,000 g of methylene chloride was added. Then triphenylsulfonium chloride aqueous solution was added to the solution, which was stirred for 30 minutes. The organic layer was taken out, washed twice with 300 g of water, concentrated, and purified by chromatography. There was obtained 22.4 g (yield 40%) of the target compound, designated Salt-5.

[2] Synthesis of Polymers

Synthesis Example 1

Synthesis of Polymer 1

A 3-L flask was charged with 314.4 g of 4-acetoxystyrene, 22.0 g of 4-chlorostyrene, 190.7 g of indene, and 675 g of toluene as solvent. The reactor was cooled at −70° C. in nitrogen atmosphere, after which vacuum pumping and nitrogen flow were repeated three times. The reactor was warmed up to room temperature, whereupon 40.5 g of 2,2'-azobis(2,4-dimethylvaleronitrile) (V-65 by Wako Pure Chemical Industries, Ltd.) was added as polymerization initiator. The reactor was heated at 45° C., whereupon reaction ran for 20 hours. The reactor was further heated at 55° C. whereupon reaction ran for further 20 hours. The reaction solution was concentrated to 1/2 in volume. The concentrate was poured to 15.0 L of methanol for precipitation. A white solid was collected by filtration and vacuum dried at 40° C., obtaining 309 g of a white polymer.

The polymer was again dissolved in a mixture of 488 g of methanol and 540 g of THF. 162 g of triethylamine and 32 g of water were added to the solution, whereupon deprotection reaction was carried out at 60° C. for 40 hours. The reaction solution was concentrated and dissolved in 870 g of ethyl acetate. The solution was subjected to once neutralization/separation/washing with a mixture of 250 g of water and 98 g of acetic acid, once separation/washing with a mixture of 225 g of water and 75 g of pyridine, and 4 times separation/washing with 225 g of water. The upper layer, ethyl acetate solution was concentrated, dissolved in 250 g of acetone, and poured into 15 L of water for precipitation. The precipitate was filtered and vacuum dried at 50° C. for 40 hours, obtaining 223 g of a white polymer.

The polymer was analyzed by $^{13}$C-NMR, $^1$H-NMR and GPC, with the results shown below.

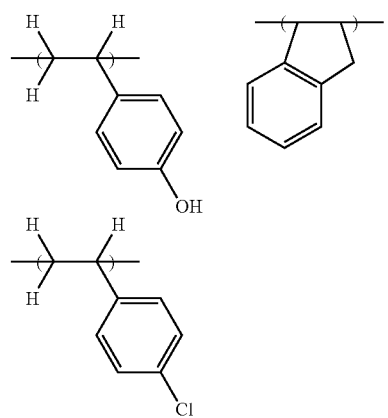

| Copolymer compositional ratio | 80.0 | 10.0 | 10.0 |

Mw=4,500
Mw/Mn=1.65

Synthesis Example 2

Synthesis of Polymer 7

In nitrogen atmosphere, 890 g of 50.0 wt % PGMEA solution of 4-hydroxystyrene, 47.7 g of acenaphthylene, 310 g of 54.7 wt % PGMEA solution of 4-(2-hydroxy-2-propyl)-styrene, 87.0 g of triphenylsulfonium 1,1,3,3,3-pentafluoro-2-methacryloyloxypropane-1-sulfonate, 96.1 g of dimethyl 2,2'-azobis(2-methylpropionate) (V-601 by Wako Pure Chemical Industries, Ltd.), and 360 g of γ-butyrolactone and 220 g of PGMEA as solvent were fed into a 3000-mL dropping cylinder to form a monomer solution. In nitrogen atmosphere, a 5000-mL polymerization flask was charged with 580 g of γ-butyrolactone, which was heated at 80° C. The monomer solution was added dropwise from the dropping cylinder to the flask over 4 hours. After the completion of dropwise addition, the polymerization solution was continuously stirred for 18 hours while maintaining its temperature at 80° C. The polymerization solution was cooled to room temperature and added dropwise to 22.5 kg of diisopropyl ether whereupon the copolymer agglomerated. Diisopropyl ether was decanted off, and the copolymer was dissolved in 2,250 g of acetone. The acetone solution was added dropwise to 22.5 kg of diisopropyl ether whereupon the copolymer precipitated. The copolymer precipitate was collected by filtration and dissolved in 2,250 g of acetone again. The acetone solution was added dropwise to 22.5 kg of water. The copolymer precipitate was collected by filtration and dried at 40° C. for 40 hours, obtaining 700 g of a white polymer.

The polymer designated Polymer 7 was analyzed by $^{13}$C-NMR, $^{1}$H-NMR and GPC, with the results shown below.

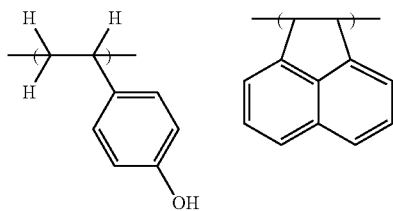

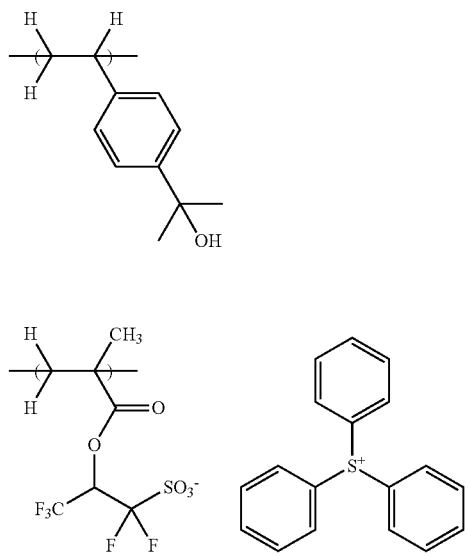

| Copolymer compositional ratio | 66.0 | 9.0 | 21.5 | 3.5 |

Mw=13,000
Mw/Mn=1.62

Synthesis Examples 3 to 13

Synthesis of Polymers 2 to 6, 8 to 13

Polymers 2 to 6 were synthesized by the same procedures as in Synthesis Example 1 except that the type and amount (molar ratio) of monomers were changed. Polymers 8 to 13 were synthesized by the same procedures as in Synthesis Example 2 except that the type and amount (molar ratio) of monomers were changed.

For Polymers 1 to 13, the type and molar ratio of monomers are tabulated in Table 1. The structures of recurring units incorporated in the polymers are shown in Tables 2 to 5.

TABLE 1

| | Unit 1 | Ratio (mol %) | Unit 2 | Ratio (mol %) | Unit 3 | Ratio (mol %) | Unit 4 | Ratio (mol %) | Mw | Mw/Mn |
|---|---|---|---|---|---|---|---|---|---|---|
| Polymer 1 | A-1 | 80.0 | B-1 | 10.0 | B-4 | 10.0 | | | 4,500 | 1.65 |
| Polymer 2 | A-1 | 80.0 | B-2 | 8.0 | B-3 | 12.0 | | | 4,200 | 1.64 |
| Polymer 3 | A-1 | 60.0 | B-2 | 10.0 | C-1 | 30.0 | | | 4,300 | 1.62 |
| Polymer 4 | A-1 | 35.0 | B-2 | 10.0 | C-2 | 55.0 | | | 3,800 | 1.61 |
| Polymer 5 | A-1 | 45.0 | B-2 | 10.0 | C-3 | 45.0 | | | 4,100 | 1.63 |
| Polymer 6 | A-1 | 55.0 | B-3 | 15.0 | C-1 | 30.0 | | | 4,000 | 1.62 |
| Polymer 7 | A-1 | 66.0 | B-2 | 9.0 | C-1 | 21.5 | P-1 | 3.5 | 13,000 | 1.62 |
| Polymer 8 | A-1 | 71.0 | B-2 | 10.0 | C-1 | 15.0 | P-2 | 4.0 | 14,000 | 1.65 |
| Polymer 9 | A-1 | 68.0 | B-2 | 9.0 | C-1 | 20.0 | P-3 | 3.0 | 14,000 | 1.64 |
| Polymer 10 | A-1 | 66.0 | B-2 | 10.0 | C-1 | 21.0 | P-4 | 3.0 | 16,000 | 1.63 |
| Polymer 11 | A-1 | 52.0 | B-2 | 10.0 | C-2 | 34.5 | P-1 | 3.5 | 16,000 | 1.63 |
| Polymer 12 | A-1 | 56.5 | B-2 | 9.0 | C-3 | 31.0 | P-1 | 3.5 | 15,000 | 1.62 |
| Polymer 13 | A-2 | 60.0 | B-3 | 9.0 | C-1 | 27.5 | P-1 | 3.5 | 16,000 | 1.62 |

TABLE 2
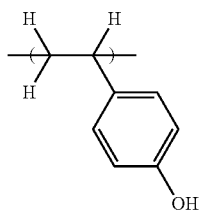 A-1
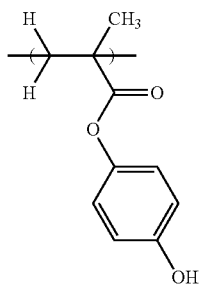 A-2
TABLE 3
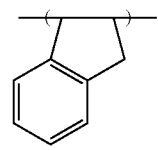 B-1
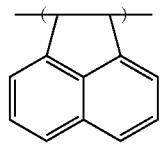 B-2
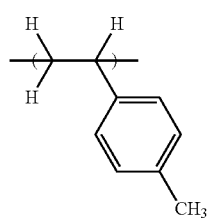 B-3
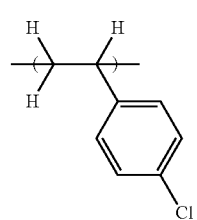 B-4
TABLE 4
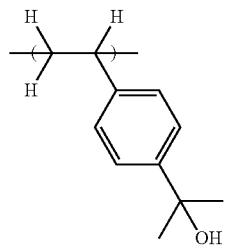 C-1
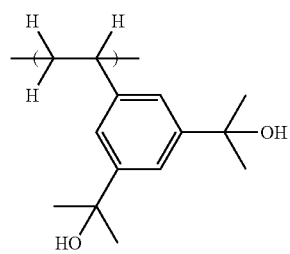 [SMILES: CCC(C)c1cc(C(C)(C)O)cc(C(C)(C)O)c1] C-2
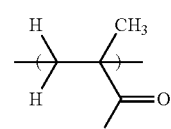 C-3
TABLE 5
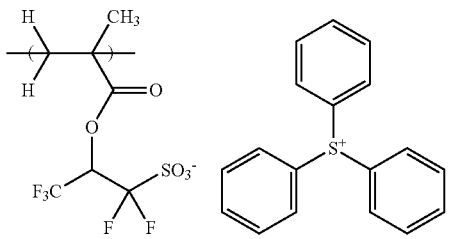 P-1
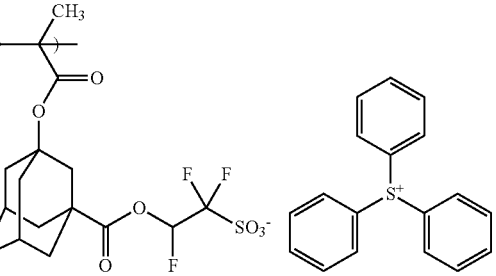 P-2
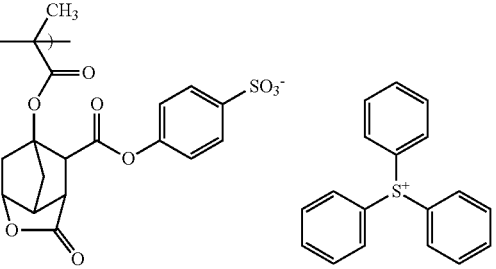 P-3

TABLE 5-continued

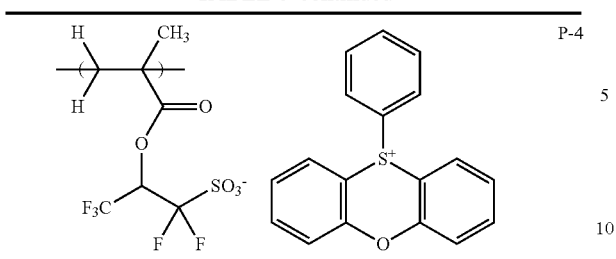

P-4

[3] Preparation of Negative Resist Compositions

Examples 2-1 to 2-23 and Comparative Examples 1-1 to 1-7

Negative resist compositions in solution form were prepared by dissolving a polymer (Polymers 1 to 13), an acid generator (PAG-1 to PAG-4), a onium salt (Salt-1 to Salt-5) or comparative quencher (Q-1 to Q-3) as quencher, and tetramethoxymethylglycoluril (TMGU) as crosslinker in an organic solvent in accordance with the formulation shown in Tables 6 and 7, and filtering through a filter with a pore size of 0.2 μm or a nylon or UPE filter with a pore size of 0.02 μm. The solvents used were propylene glycol monomethyl ether acetate (PGMEA), ethyl lactate (EL), and propylene glycol monomethyl ether (PGME). All the compositions contained 0.075 pbw of surfactant PF-636 (Omnova Solutions).

TABLE 6

|  |  | Resist composition | Resin (pbw) | Acid generator (pbw) | Quencher (pbw) | Crosslinker (pbw) | Solvent 1 (pbw) | Solvent 2 (pbw) | Solvent 3 (pbw) |
|---|---|---|---|---|---|---|---|---|---|
| Example | 2-1 | R-1 | Polymer 1 (80) | PAG-1 (8) PAG-3 (2) | Salt-1 (4.0) | TMGU (8.2) | PGMEA (1,080) | EL (1,080) | PGME (1,440) |
|  | 2-2 | R-2 | Polymer 1 (80) | PAG-1 (8) PAG-3 (2) | Salt-2 (4.1) | TMGU (8.2) | PGMEA (1,080) | EL (1,080) | PGME (1,440) |
|  | 2-3 | R-3 | Polymer 1 (80) | PAG-1 (8) PAG-3 (2) | Salt-3 (4.2) | TMGU (8.2) | PGMEA (1,080) | EL (1,080) | PGME (1,440) |
|  | 2-4 | R-4 | Polymer 1 (80) | PAG-1 (8) PAG-3 (2) | Salt-4 (4.0) | TMGU (8.2) | PGMEA (1,080) | EL (1,080) | PGME (1,440) |
|  | 2-5 | R-5 | Polymer 2 (80) | PAG-1 (8) | Salt-1 (4.2) | TMGU (8.2) | PGMEA (1,080) | EL (1,080) | PGME (1.440) |
|  | 2-6 | R-6 | Polymer 2 (80) | PAG-1 (8) | Salt-4 4.2) | TMGU (8.2) | PGMEA (1,080) | EL (1,080) | PGME (1,440) |
|  | 2-7 | R-7 | Polymer 3 (80) | PAG-1 (8) | Salt-1 (4.1) |  | PGMEA (1,080) | EL (1,080) | PGME (1,440) |
|  | 2-8 | R-8 | Polymer 4 (80) | PAG-1 (8) | Salt-1 (4.2) |  | PGMEA (1,080) | EL (1,080) | PGME (1,440) |
|  | 2-9 | R-9 | Polymer 5 (80) | PAG-2 (8) | Salt-2 (4.0) |  | PGMEA (1,080) | EL (1,080) | PGME (1,440) |
|  | 2-10 | R-10 | Polymer 6 (80) | PAG-4 (8) | Salt-1 (4.3) |  | PGMEA (1,080) | EL (1,080) | PGME (1,440) |
|  | 2-11 | R-11 | Polymer 7 (80) | PAG-1 (8) | Salt-3 (4.1) |  | PGMEA (1,080) | EL (1,080) | PGME (1,440) |
|  | 2-12 | R-12 | Polymer 8 (80) |  | Salt-3 (4.2) |  | PGMEA (1,080) | EL (1,080) | PGME (1,440) |
|  | 2-13 | R-13 | Polymer 9 (80) | PAG-4 (8) | Salt-1 (4.3) |  | PGMEA (1,080) | EL (1,080) | PGME (1,440) |
|  | 2-14 | R-14 | Polymer 10 (80) | PAG-1 (8) | Salt-2 (4.1) |  | PGMEA (1,080) | EL (1,080) | PGME (1,440) |
|  | 2-15 | R-15 | Polymer 11 (80) |  | Salt-1 (4.2) |  | PGMEA (1,080) | EL (1,080) | PGME (1,440) |
|  | 2-16 | R-16 | Polymer 12 (80) | PAG-1 (8) PAG-3 (2) | Salt-4 (4.2) |  | PGMEA (1,080) | EL (1.080) | PGME (1,440) |
|  | 2-17 | R-17 | Polymer 13 (80) |  | Salt-1 (4.1) |  | PGMEA (1,080) | EL (1,080) | PGME (1,440) |
|  | 2-18 | R-18 | Polymer 3 (80) Polymer 7 (80) | PAG-1 (5) PAG-2 (2) | Salt-1 (4.3) |  | PGMEA (1,080) | EL (1,080) | PGME (1,440) |

TABLE 6-continued

| | Resist composition | Resin (pbw) | Acid generator (pbw) | Quencher (pbw) | Crosslinker (pbw) | Solvent 1 (pbw) | Solvent 2 (pbw) | Solvent 3 (pbw) |
|---|---|---|---|---|---|---|---|---|
| 2-19 | R-19 | Polymer 4 (80) Polymer 11 (80) | PAG-1 (4) PAG-2 (4) | Salt-1 (4.2) | | PGMEA (1,080) | EL (1,080) | PGME (1,440) |
| 2-20 | R-20 | Polymer 5 (80) Polymer 12 (80) | PAG-4 (8) | Salt-2 (4.3) | | PGMEA (1.080) | EL (1.080) | PGME (1,440) |
| 2-21 | R-21 | Polymer 6 (80) Polymer 13 (80) | PAG-1 (4) PAG-2 (4) | Salt-4 (4.4) | | PGMEA (1,080) | EL (1,080) | PGME (1,440) |
| 2-22 | R-22 | Polymer 1 (80) | PAG-1 (8) PAG-3 (2) | Salt-5 (4.3) | TMGU (8.2) | PGMEA (1,080) | EL (1,080) | PGME (1,440) |
| 2-23 | R-23 | Polymer 3 (80) Polymer 7 (80) | PAG-1 (5) PAG-2 (2) | Salt-5 (4.2) | | PGMEA (1,080) | EL (1,080) | PGME (1,440) |

TABLE 7

| | | Resist composition | Resin (pbw) | Acid generator (pbw) | Quencher (pbw) | Crosslinker (pbw) | Solvent 1 (pbw) | Solvent 2 (pbw) | Solvent 3 (pbw) |
|---|---|---|---|---|---|---|---|---|---|
| Comparative Example | 1-1 | CR-1 | Polymer 1 (80) | PAG-1 (8) PAG-3 (2) | Q-1 (4.0) | TMGU (8.2) | PGMEA (1,080) | EL (1,080) | PGME (1,440) |
| | 1-2 | CR-2 | Polymer 1 (80) | PAG-1 (8) PAG-3 (2) | Q-2 (5.8) | TMGU (8.2) | PGMEA (1,080) | EL (1,080) | PGME (1,440) |
| | 1-3 | CR-3 | Polymer 1 (80) | PAG-1 (8) PAG-3 (2) | Q-3 (2.3) | TMGU (8.2) | PGMEA (1,080) | EL (1,080) | PGME (1,440) |
| | 1-4 | CR-4 | Polymer 3 (80) | PAG-1 (8) | Q-1 (4.4) | | PGMEA (1,080) | EL (1,080) | PGME (1,440) |
| | 1-5 | CR-5 | Polymer 3 (80) | PAG-1 (8) | Q-2 (5.5) | | PGMEA (1,080) | EL (1,080) | PGME (1,440) |
| | 1-6 | CR-6 | Polymer 3 (80) Polymer 7 (80) | PAG-1 (5) PAG-2 (2) | Q-1 (4.4) | | PGMEA (1,080) | EL (1,080) | PGME (1,440) |
| | 1-7 | CR-7 | Polymer 3 (80) Polymer 7 (80) | PAG-1 (5) PAG-2 (2) | Q-2 (5.8) | | PGMEA (1,080) | EL (1,080) | PGME (1,440) |

In Tables 6 and 7, Salt-1 to Salt-5, Q-1 to Q-3, and PAG-1 to PAG-4 have the following structure.

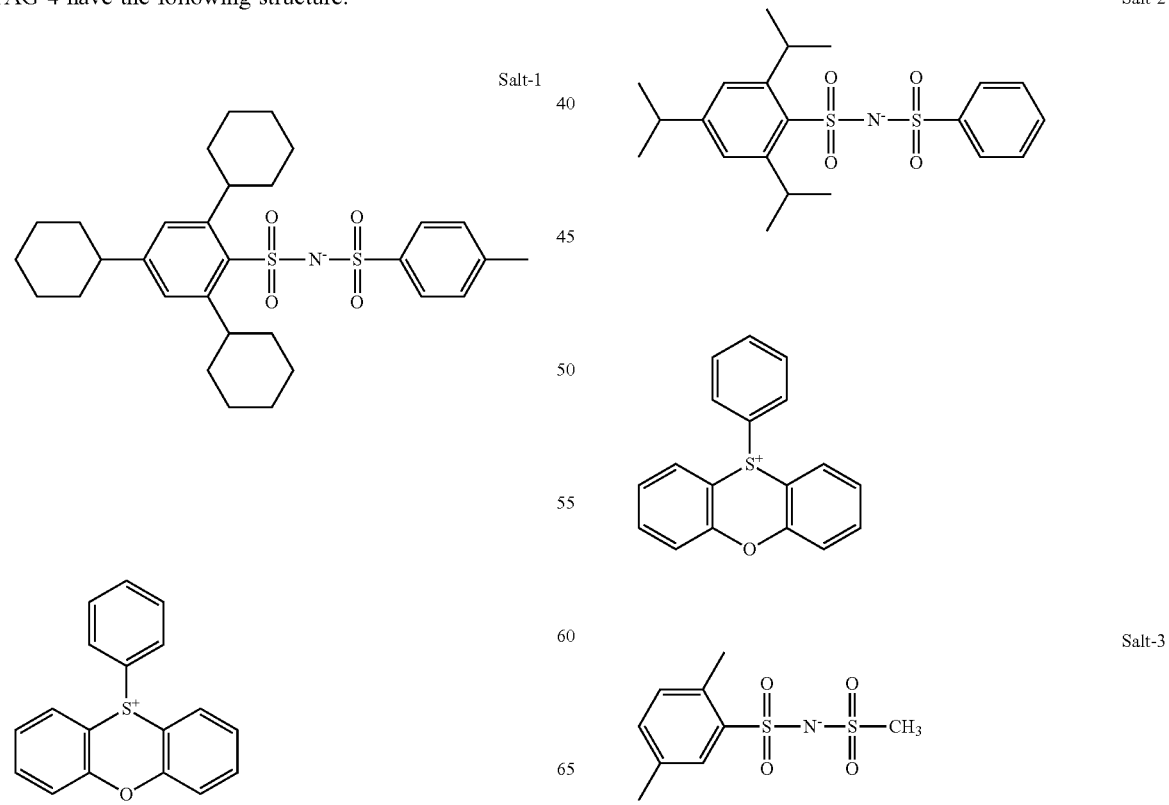

-continued
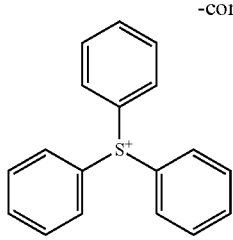
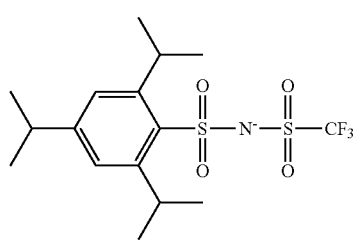
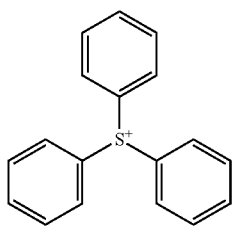
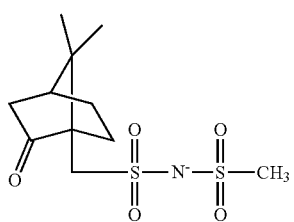
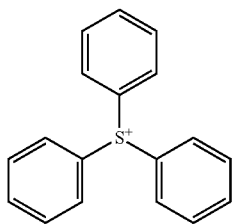
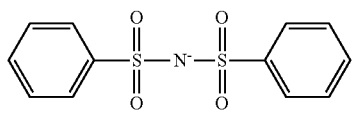
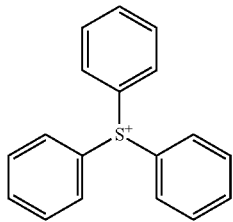
-continued
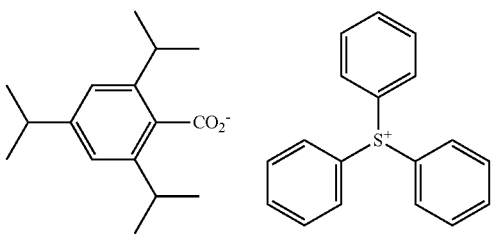
Q-2
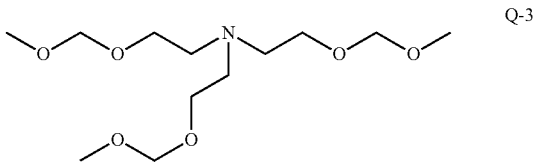
Q-3
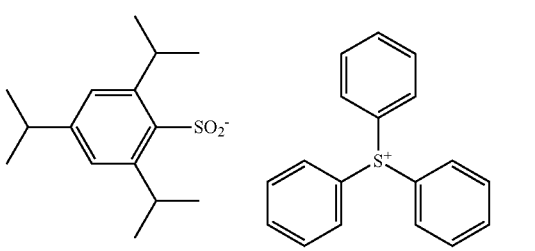
PAG-1
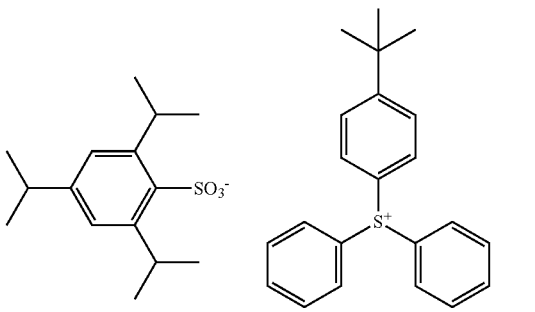
PAG-2
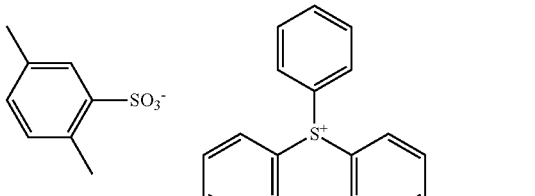
PAG-3
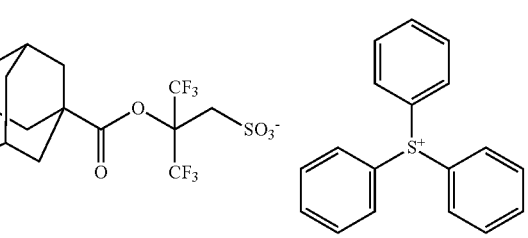
PAG-4
Salt-4
Salt-5
Q-1

[4] EB Writing Test

Examples 3-1 to 3-23 and Comparative Examples 2-1 to 2-7

Using a coater/developer system ACT-M (Tokyo Electron Ltd.), each of the negative resist compositions (R-1 to R-23 and CR-1 to CR-7) was spin coated on a mask blank of 152 mm squares having a chromium oxynitride film at the outermost surface, and prebaked on a hotplate at 110° C. for 600 seconds to form a resist film of 80 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to electron beam using an EB writer system EBM-5000Plus (NuFlare Technology Inc., accelerating voltage 50 kV), then baked (PEB) at 120° C. for 600 seconds, and developed in a 2.38 wt % tetramethylammonium hydroxide (TMAH) aqueous solution, thereby yielding negative patterns.

The patterned mask blank was observed under a top-down scanning electron microscope (TDSEM). The optimum dose (Eop) was defined as the exposure dose ($\mu C/cm^2$) which provided a 1:1 resolution at the top and bottom of a 400-nm 1:1 line-and-space pattern. The LS resolution (or maximum resolution) was defined as the minimum size of a pattern that could be resolved at the exposure dose capable of resolving a 400-nm LS pattern at 1:1. The LER of a 200-nm L/S pattern was measured under SEM. The maximum resolutions (IL resolution and IS resolution) of an isolated line (IL) and an isolated space (IS) were also measured. Notably, IL is the resolution of an isolated single line feature, and IS is the resolution of an isolated single space feature. The pattern was visually observed to judge whether or not the pattern profile was rectangular.

The test results are shown in Table 8.

TABLE 8

| | | Resist composition | Eop L/S ($\mu C/cm^2$) | LS resolution (nm) | IL resolution (nm) | IS resolution (nm) | LER (nm) | Pattern profile |
|---|---|---|---|---|---|---|---|---|
| Example | 3-1 | R-1 | 49 | 40 | 35 | 40 | 4.5 | rectangular |
| | 3-2 | R-2 | 52 | 40 | 40 | 35 | 4.8 | rectangular |
| | 3-3 | R-3 | 51 | 35 | 40 | 40 | 4.7 | rectangular |
| | 3-4 | R-4 | 53 | 40 | 35 | 40 | 4.9 | rectangular |
| | 3-5 | R-5 | 50 | 40 | 40 | 35 | 4.6 | rectangular |
| | 3-6 | R-6 | 52 | 35 | 40 | 40 | 4.8 | rectangular |
| | 3-7 | R-7 | 50 | 40 | 35 | 40 | 4.7 | rectangular |
| | 3-8 | R-8 | 53 | 40 | 40 | 35 | 4.9 | rectangular |
| | 3-9 | R-9 | 51 | 35 | 40 | 40 | 4.6 | rectangular |
| | 3-10 | R-10 | 54 | 35 | 40 | 40 | 4.8 | rectangular |
| | 3-11 | R-11 | 53 | 35 | 40 | 40 | 4.7 | rectangular |
| | 3-12 | R-12 | 51 | 40 | 40 | 35 | 4.9 | rectangular |
| | 3-13 | R-13 | 52 | 35 | 40 | 40 | 4.6 | rectangular |
| | 3-14 | R-14 | 52 | 40 | 35 | 40 | 4.8 | rectangular |
| | 3-15 | R-15 | 51 | 35 | 40 | 40 | 4.9 | rectangular |
| | 3-16 | R-16 | 53 | 35 | 40 | 40 | 4.7 | rectangular |
| | 3-17 | R-17 | 52 | 40 | 35 | 40 | 4.8 | rectangular |
| | 3-18 | R-18 | 51 | 35 | 35 | 40 | 4.9 | rectangular |
| | 3-19 | R-19 | 52 | 35 | 35 | 40 | 4.7 | rectangular |
| | 3-20 | R-20 | 52 | 35 | 35 | 40 | 4.8 | rectangular |
| | 3-21 | R-21 | 52 | 35 | 40 | 35 | 4.6 | rectangular |
| | 3-22 | R-22 | 51 | 35 | 40 | 40 | 4.9 | rectangular |
| | 3-23 | R-23 | 50 | 40 | 35 | 40 | 4.8 | rectangular |
| Comparative Example | 2-1 | CR-1 | 50 | 60 | 55 | 50 | 6.1 | rectangular |
| | 2-2 | CR-2 | 53 | 50 | 45 | 50 | 5.8 | rectangular |
| | 2-3 | CR-3 | 51 | 50 | 50 | 50 | 6.2 | rectangular |
| | 2-4 | CR-4 | 52 | 50 | 55 | 55 | 5.7 | rectangular |
| | 2-5 | CR-5 | 50 | 55 | 50 | 50 | 5.8 | rectangular |
| | 2-6 | CR-6 | 53 | 55 | 50 | 50 | 5.9 | rectangular |
| | 2-7 | CR-7 | 54 | 50 | 55 | 50 | 6.0 | rectangular |

All the inventive resist compositions (Examples 3-1 to 3-23) comprising the inventive onium salts show satisfactory results with respect to resolution, rectangular pattern profile, and LER. The resist compositions of Comparative Examples 2-1 to 2-7 are inferior in resolution and LER to Examples.

It has been demonstrated that by using the inventive resist composition to form a resist film and exposing it via high-energy radiation lithography, a pattern having high resolution and a minimal LER is formed. The resist composition forms a pattern without defects and development residues while avoiding chemical flare and local heat during high current writing. The resist pattern forming process using the inventive resist composition is useful in the photolithography for the fabrication of microelectronic devices, especially processing of photomask blanks.

Japanese Patent Application No. 2018-200797 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An onium salt having the formula (A):

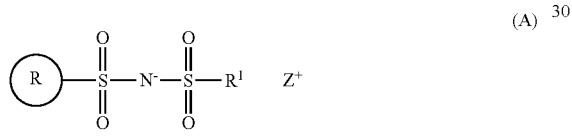
(A)

wherein $R^1$ is a $C_1$-$C_{20}$ monovalent hydrocarbon group which may contain a heteroatom,
the ring R is a group having the formula (A1),

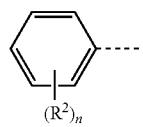
(A1)

wherein the broken line designates a valence bond, $R^2$ is each independently a $C_1$-$C_{20}$ monovalent hydrocarbon group, at least one $R^2$ is bonded at the ortho-position relative to the carbon atom bonded to the sulfonyl group, n is an integer of 2 to 5,
$Z^+$ is a sulfonium cation having the formula (A2) or iodonium cation having the formula (A3):

(A2)
(A3)

wherein $R^3$ to $R^7$ are each independently a $C_1$-$C_{20}$ monovalent hydrocarbon group which may contain a heteroatom, any two or more of $R^3$, $R^4$ and $R^5$ may bond together to form a ring with the sulfur atom to which they are attached.

2. The onium salt of claim 1 wherein $R^2$ is a $C_3$-$C_{20}$ branched or cyclic monovalent hydrocarbon group.

3. The onium salt of claim 1 wherein n is an integer of 3 to 5.

4. The onium salt of claim 1 wherein $R^2$ is a $C_3$-$C_{20}$ cyclic monovalent hydrocarbon group.

5. The onium salt of claim 1 wherein the anion in the onium salt having formula (A) is selected from the group consisting of the following formulae:

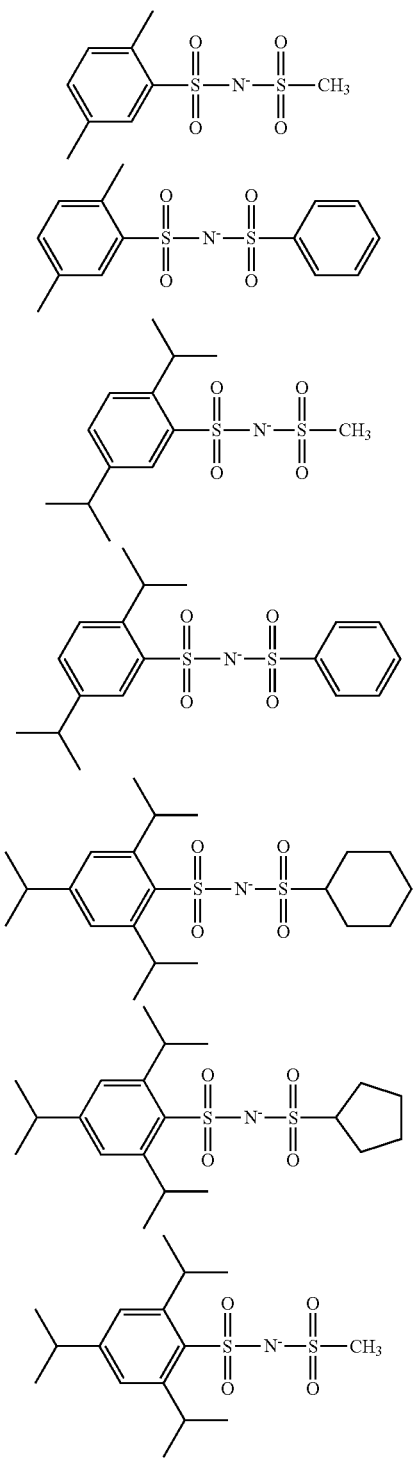

-continued
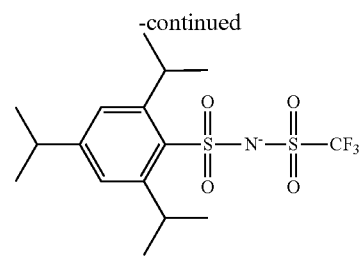
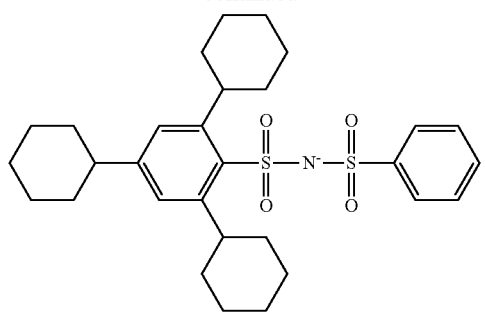
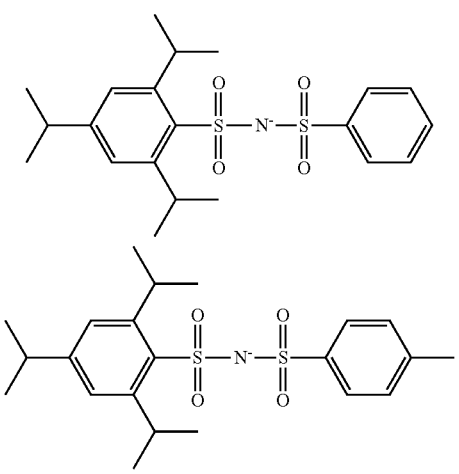
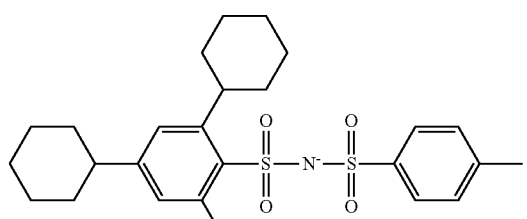
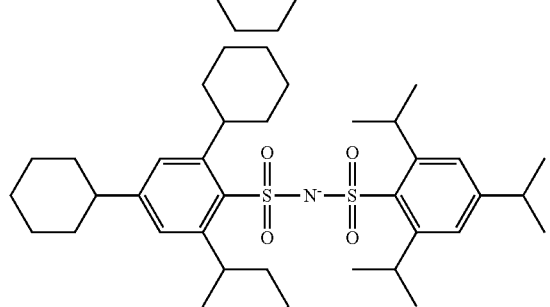
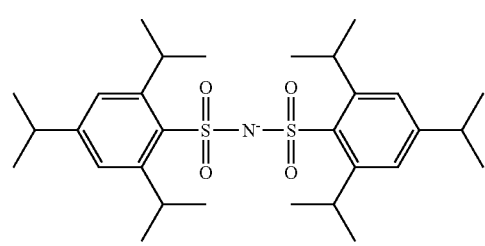
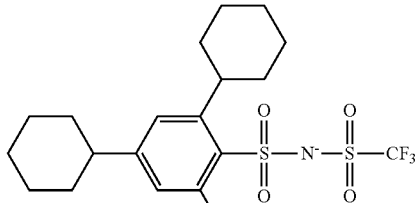
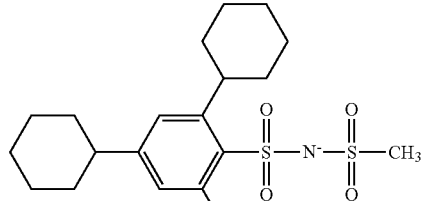
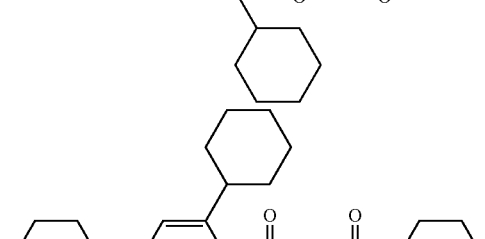
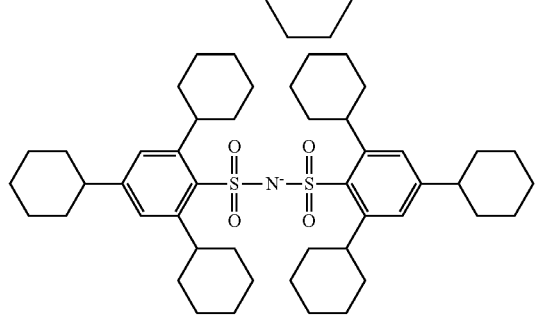
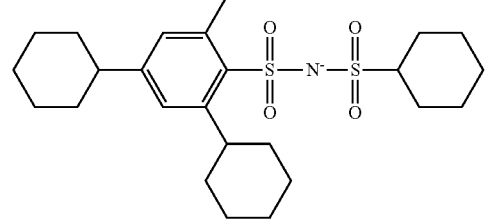
6. A negative resist composition comprising (A) the onium salt of claim 1, and (B) a base polymer containing a polymer comprising recurring units having the formula (B1):

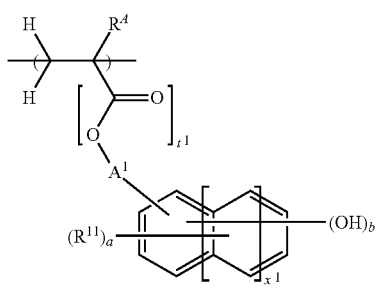

(B1)

wherein $R^A$ is hydrogen, fluorine, methyl or trifluoromethyl, $R^{11}$ is each independently halogen, an optionally halogenated $C_2$-$C_8$ acyloxy group, optionally halogenated $C_1$-$C_6$ alkyl group, or optionally halogenated $C_1$-$C_6$ alkoxy group, $A^1$ is a single bond or $C_1$-$C_{10}$ alkanediyl group in which an ether bond may intervene in a carbon-carbon bond, $t^1$ is 0 or 1, $x^1$ is an integer of 0 to 2, a is an integer satisfying $0 \le 5 \le 2x^1-b$, and b is an integer of 1 to 5.

7. The negative resist composition of claim 6 wherein the polymer further comprises recurring units of at least one type selected from recurring units having the formulae (B2), (B3) and (B4):

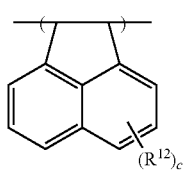

(B2)

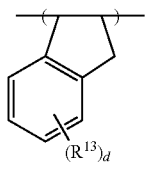

(B3)

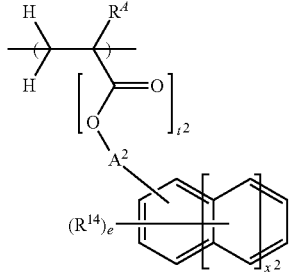

(B4)

wherein $R^A$ is hydrogen, fluorine, methyl or trifluoromethyl, $R^{12}$ and $R^{13}$ are each independently hydroxyl, halogen, acetoxy, an optionally halogenated $C_1$-$C_8$ alkyl group, optionally halogenated $C_1$-$C_8$ primary alkoxy group, $C_2$-$C_8$ secondary alkoxy group, optionally halogenated $C_2$-$C_8$ acyloxy group, or optionally halogenated $C_2$-$C_8$ alkylcarbonyloxy group, $R^{14}$ is an acetyl group, acetoxy group, $C_1$-$C_{20}$ alkyl group, $C_1$-$C_{20}$ primary alkoxy group, $C_2$-$C_{20}$ secondary alkoxy group, $C_2$-$C_{20}$ acyloxy group, $C_2$-$C_{20}$ alkoxyalkyl group, $C_2$-$C_{20}$ alkylthioalkyl group, halogen atom, nitro group, or cyano group, $A^2$ is a single bond or $C_1$-$C_{10}$ alkanediyl group in which an ether bond may intervene in a carbon-carbon bond, c and d are each independently an integer of 0 to 4, e is an integer of 0 to 5, $x^2$ is an integer of 0 to 2, and $t^2$ is 0 or 1.

8. The negative resist composition of claim 6 wherein the polymer further comprises recurring units having the formula (B5):

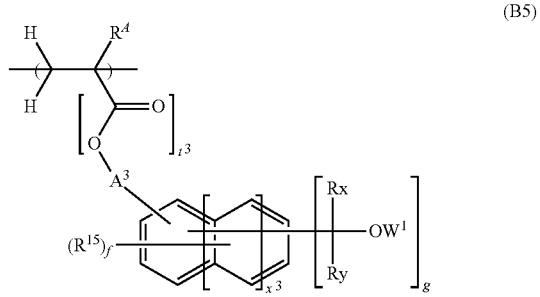

(B5)

wherein $R^A$ is hydrogen, fluorine, methyl or trifluoromethyl, $R^{15}$ is each independently halogen, an optionally halogenated $C_2$-$C_8$ acyloxy group, optionally halogenated $C_1$-$C_6$ alkyl group, or optionally halogenated $C_1$-$C_6$ alkoxy group, $A^3$ is a single bond or $C_1$-$C_{10}$ alkanediyl group in which an ether bond may intervene in a carbon-carbon bond, $W^1$ is hydrogen, a $C_1$-$C_{10}$ monovalent aliphatic hydrocarbon group in which an ether bond, carbonyl moiety or carbonyloxy moiety may intervene in a carbon-carbon bond, or an optionally substituted monovalent aromatic ring group, Rx and Ry are each independently hydrogen, an optionally hydroxy or alkoxy-substituted $C_1$-$C_{15}$ alkyl group or an optionally substituted monovalent aromatic ring group, with the proviso that both Rx and Ry are not hydrogen at the same time, Rx and Ry may bond together to form a ring with the carbon atom to which they are attached, $x^3$ is an integer of 0 to 2, $t^3$ is 0 or 1, f is an integer satisfying $0 \le f \le 5+2x^3-g$, and g is an integer of 1 to 3.

9. The negative resist composition of claim 8 wherein the polymer further comprises recurring units of at least one type selected from recurring units having the formulae (B6), (B7) and (B8):

(B6)

-continued

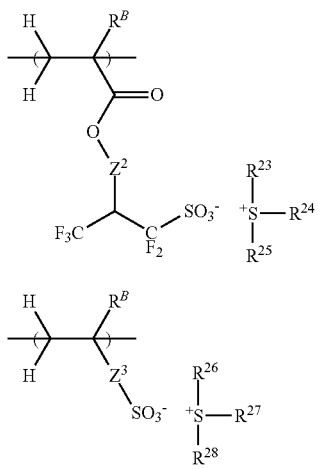

(B7)

(B8)

wherein $R^B$ is each independently hydrogen or methyl, $Z^1$ is a single bond, phenylene group, —O—$Z^{11}$—, —C(=O)—O—$Z^{11}$—, or —C(=O)—NH—$Z^{11}$—, $Z^{11}$ is a $C_1$-$C_6$ alkanediyl, $C_2$-$C_6$ alkenediyl or phenylene group, which may contain a carbonyl moiety, ester bond, ether bond or hydroxyl moiety, $Z^2$ is a single bond or —$Z^{21}$—C(=O)—O—, $Z^{21}$ is a $C_1$-$C_{20}$ divalent hydrocarbon group which may contain a heteroatom, $Z^3$ is a single bond, methylene, ethylene, phenylene, fluorinated phenylene, —O—$Z^{31}$—, —C(=O)—O—$Z^{31}$—, or —C(=O)—NH—$Z^{31}$—, $Z^{31}$ is a $C_1$-$C_6$ alkanediyl, $C_2$-$C_6$ alkenediyl or phenylene group, which may contain a carbonyl moiety, ester bond, ether bond or hydroxyl moiety, $R^{21}$ to $R^{28}$ are each independently a $C_1$-$C_{20}$ monovalent hydrocarbon group which may contain a heteroatom, or $R^{21}$ and $R^{22}$ may bond together to form a ring with the sulfur atom to which they are attached, or any two or more of $R^{23}$, $R^{24}$ and $R^{25}$ may bond together to form a ring with the sulfur atom to which they are attached, any two or more of $R^{26}$, $R^{27}$ and $R^{28}$ may bond together to form a ring with the sulfur atom to which they are attached, and $M^-$ is a non-nucleophilic counter ion.

10. The negative resist composition of claim 9 wherein the base polymer (B) further contains a polymer free of recurring units having the formula (B6), recurring units having the formula (B7), and recurring units having the formula (B8).

11. The negative resist composition of claim 8, which is free of a crosslinker.

12. The negative resist composition of claim 6 wherein the polymer comprises recurring units having the formula (B1-1), recurring units having the formula (B5-1), and recurring units having the formula (B7):

(B1-1)

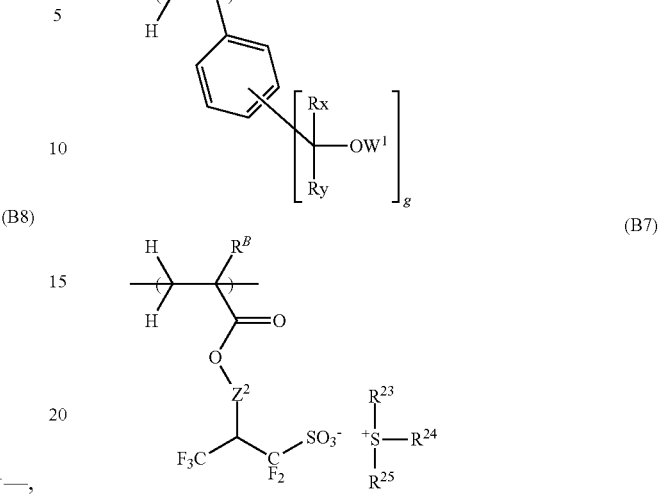

(B5-1)

(B7)

wherein $R^A$ is each independently hydrogen, fluorine, methyl or trifluoromethyl, $R^B$ is hydrogen or methyl, $W^1$ is hydrogen, a $C_1$-$C_{10}$ monovalent aliphatic hydrocarbon group in which an ether bond, carbonyl moiety or carbonyloxy moiety may intervene in a carbon-carbon bond, or an optionally substituted monovalent aromatic ring group, Rx and Ry are each independently hydrogen, an optionally hydroxy or alkoxy-substituted $C_1$-$C_{15}$ alkyl group or an optionally substituted monovalent aromatic ring group, with the proviso that both Rx and Ry are not hydrogen at the same time, Rx and Ry may bond together to form a ring with the carbon atom to which they are attached, $Z^2$ is a single bond or —$Z^{21}$—C(=O)—O—, $Z^{21}$ is a $C_1$-$C_{20}$ divalent hydrocarbon group which may contain a heteroatom, $R^{23}$ to $R^{25}$ are each independently a $C_1$-$C_{20}$ monovalent hydrocarbon group which may contain a heteroatom, or any two or more of $R^{23}$, $R^{24}$ and $R^{25}$ may bond together to form a ring with the sulfur atom to which they are attached, b' is an integer of 1 to 3, and g is an integer of 1 to 3.

13. The negative resist composition of claim 6, further comprising (C) a crosslinker.

14. The negative resist composition of claim 6, further comprising (E) an acid generator.

15. A photomask blank coated with the negative resist composition of claim 6.

16. A resist pattern forming process comprising the steps of:
applying the negative resist composition of claim 6 onto a substrate to form a resist film thereon,
exposing the resist film patternwise to high-energy radiation, and
developing the resist film in an alkaline developer to form a resist pattern.

17. The process of claim 16 wherein the high-energy radiation is EUV or EB.

18. The process of claim 16 wherein the substrate is a photomask blank.

* * * * *